United States Patent
Coleman et al.

(10) Patent No.: US 11,147,472 B2
(45) Date of Patent: Oct. 19, 2021

(54) SIDE-STREAM VOLUMETRIC CAPNOGRAPHY

(71) Applicant: Covidien LP, Mansfield, MA (US)

(72) Inventors: Joshua Lewis Coleman, Jerusalem (IL); Michal Ronen, Givat Brenner (IL)

(73) Assignee: COVIDIEN LP, Mansfield, MA (US)

( * ) Notice: Subject to any disclaimer, the term of this patent is extended or adjusted under 35 U.S.C. 154(b) by 949 days.

(21) Appl. No.: 15/595,212

(22) Filed: May 15, 2017

(65) Prior Publication Data

US 2017/0325716 A1 Nov. 16, 2017

Related U.S. Application Data

(60) Provisional application No. 62/336,663, filed on May 15, 2016.

(51) Int. Cl.
*A61B 5/08* (2006.01)
*A61B 5/083* (2006.01)
(Continued)

(52) U.S. Cl.
CPC .............. *A61B 5/082* (2013.01); *A61B 5/087* (2013.01); *A61B 5/0836* (2013.01); *A61B 5/097* (2013.01);
(Continued)

(58) Field of Classification Search
None
See application file for complete search history.

(56) References Cited

U.S. PATENT DOCUMENTS 5,069,220 A * 12/1991 Casparie ................. A61B 5/083
600/532
6,286,360 B1 * 9/2001 Drzewiecki ............ A61B 5/083
702/24

(Continued)

FOREIGN PATENT DOCUMENTS

EP  1579882 A1  9/2005
WO  2006/119546 A1  11/2006

OTHER PUBLICATIONS

Bhavani-Shankar K., et al: "Defining Segments and Phases of a Time Capnogram", Anethesia and Analgesia, Williams and Wilkins, vol. 91, No. 4, Oct. 1, 2000, pp. 973-977 (XP002562634).

(Continued)

*Primary Examiner* — Jacqueline Cheng
*Assistant Examiner* — Jairo H Portillo
(74) *Attorney, Agent, or Firm* — Cantor Colburn LLP

(57) ABSTRACT

Techniques for determining a volume of exhaled $CO_2$ as a function of time using side-stream capnography, including obtaining flow dynamics measurements of a subject from a flow sensor; obtaining $CO_2$ concentration measurements of the subject from a side-stream $CO_2$ monitor; determining a duration of time ($\Delta T_{sl}$) for a sample of gas to flow from a reference point to the side-stream $CO_2$ monitor; synchronizing in time the $CO_2$ concentration measurement with the flow dynamics measurement, based on the determined $\Delta T_{sl}$; and determining a volume of $CO_2$ exhaled as a function of time, based on the flow dynamics measurement and the synchronized $CO_2$ concentration measurement.

9 Claims, 15 Drawing Sheets

(51) Int. Cl.
- *A61B 5/087* (2006.01)
- *A61B 5/097* (2006.01)
- *A61B 5/00* (2006.01)
- *G01N 33/497* (2006.01)
- *A61B 5/091* (2006.01)
- *G01N 1/22* (2006.01)
- *A61M 16/08* (2006.01)

(52) U.S. Cl.
  CPC ......... *A61B 5/7246* (2013.01); *G01N 33/497* (2013.01); *A61B 5/091* (2013.01); *A61M 16/085* (2014.02); *A61M 16/0833* (2014.02); *A61M 2230/432* (2013.01); *G01N 1/2247* (2013.01); *G01N 2001/2297* (2013.01); *G01N 2033/4975* (2013.01)

(56) References Cited

U.S. PATENT DOCUMENTS

| | | | | |
|---|---|---|---|---|
| 2002/0169385 | A1* | 11/2002 | Heinonen | A61B 5/029 600/531 |
| 2005/0045175 | A1* | 3/2005 | McCawley | A61B 5/0813 128/200.14 |
| 2005/0066968 | A1* | 3/2005 | Shofner | A61M 15/008 128/204.18 |
| 2005/0217674 | A1* | 10/2005 | Burton | A61B 5/04 128/204.23 |
| 2005/0251060 | A1* | 11/2005 | Gollar | A61B 5/097 600/532 |
| 2013/0006134 | A1 | 1/2013 | Doyle et al. | |
| 2013/0116681 | A1* | 5/2013 | Zhang | A61B 18/1206 606/34 |
| 2013/0338489 | A1* | 12/2013 | Prisk | A61B 5/055 600/420 |
| 2015/0258299 | A1* | 9/2015 | Flanagan | A61M 16/026 128/202.16 |

OTHER PUBLICATIONS

International Search Report and Written Opinion for PCT Application No. PCT/US2017/032690 dated Sep. 14, 2017, 12 pgs.

* cited by examiner

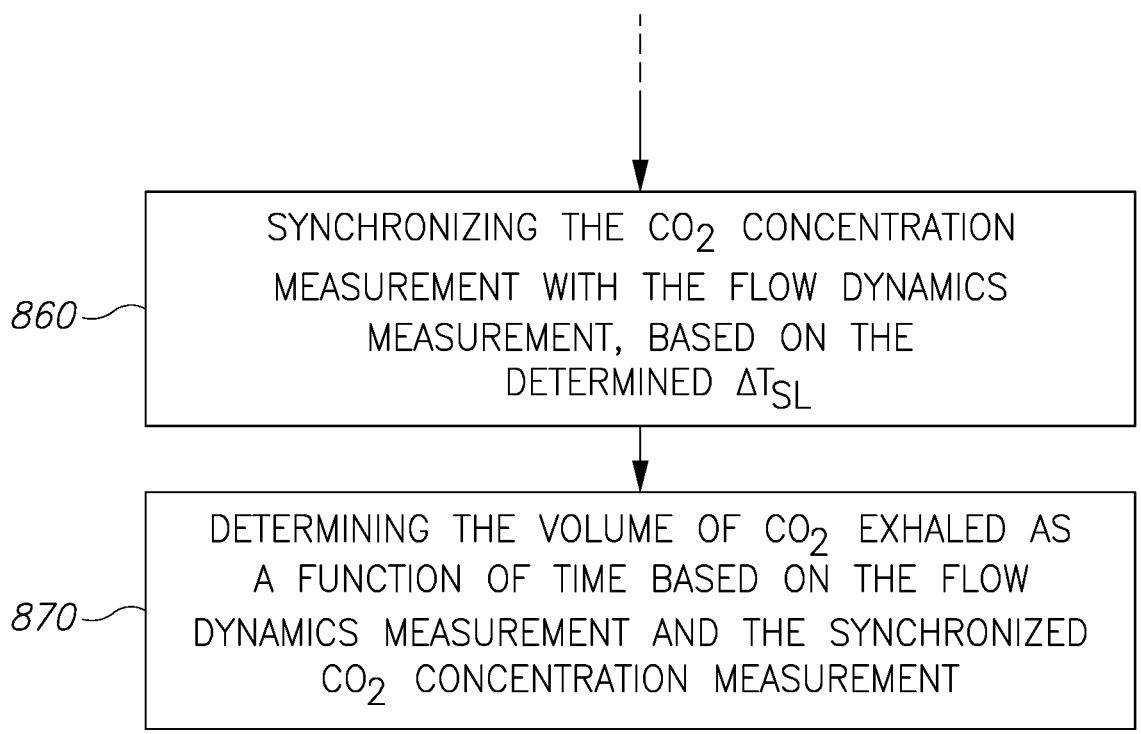
Figure 8 (cont. 1)

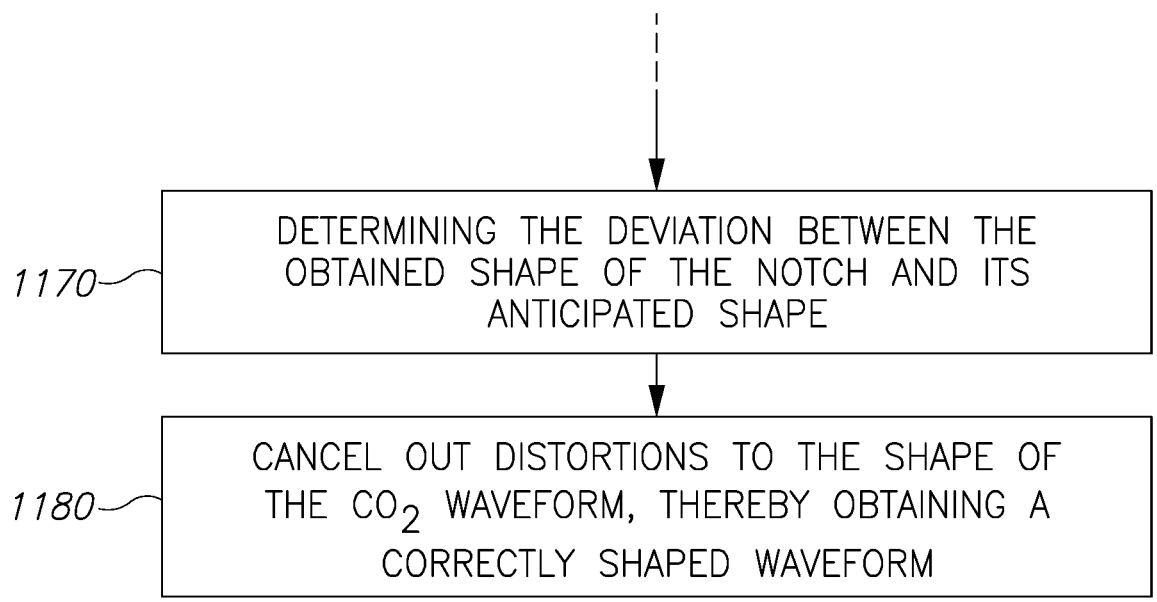
Figure 10 (cont. 1)

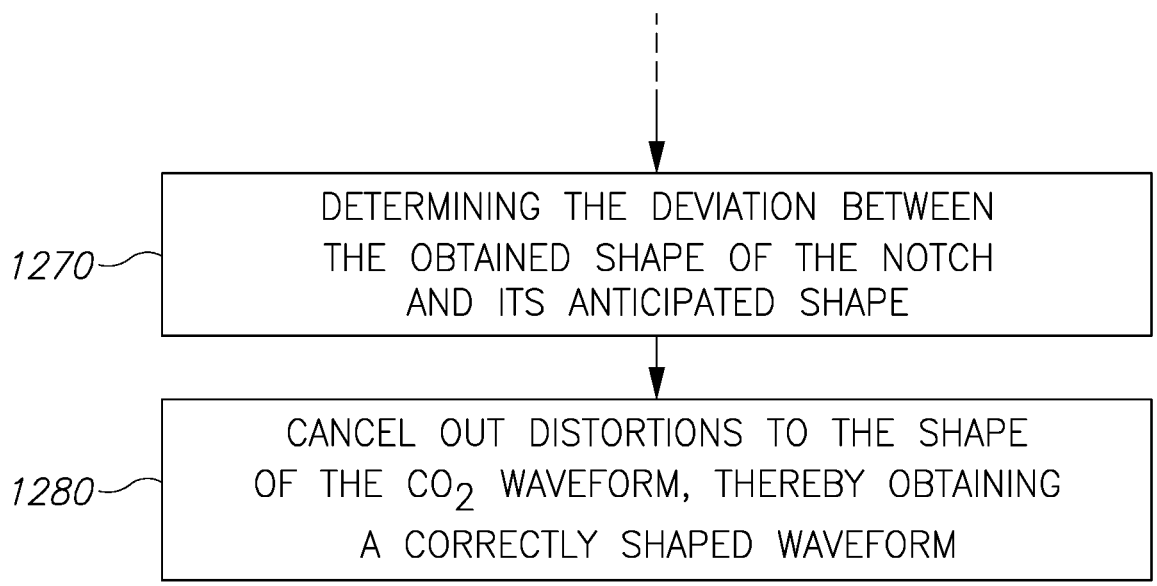
Figure 12 (cont. 1)

SIDE-STREAM VOLUMETRIC CAPNOGRAPHY

CROSS-REFERENCE TO RELATED APPLICATION(S)

This application claims priority to U.S. Provisional Patent Application No. 62/336,663, filed on May 15, 2016, which is herein incorporated by reference in its entirety.

TECHNICAL FIELD

The present disclosure generally relates to the field of capnography and, more specifically, to volumetric capnography using side-stream sampling.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Carbon dioxide ($CO_2$) concentration can be plotted against time (time capnogram) or expired volume (volumetric capnography). Volumetric capnography involves the integration of flow or volume signals with $CO_2$ concentration. That is, instantaneous $CO_2$ fractional concentration can be plotted against the expired volume, thereby facilitating an assessment of $CO_2$ elimination, alveolar dead space, and rates of emptying. Although volumetric capnography reveals important physiological information that cannot be obtained with time based capnography alone, the latter has become far more prevalent. This for two main reasons: a) time-based capnography is technically simpler, measuring only $CO_2$ concentrations; no integration of flow measurements is needed; and b) volumetric capnography is realized to date only with intubated patients and, with that, limited to main-stream capnography discussed below.

Time based capnography, can be either diverting (i.e., side-stream) or non-diverting (i.e., main-stream). In side-stream capnography airway gas samples are collected from the breathing circuit and the infrared sensor is located in a remote monitor. Breath samples are thus transported from the sampling site, through a sampling tube, to the sensor. However, side-stream systems are typically considered unable to provide meaningful comparisons between the flow and $CO_2$ waveforms because of the time delay associated with such remote sampling.

Main-stream capnography uses an in-line $CO_2$ sensor connected directly to the airway, and thus does not involve transport of breathing gases away from the sampling site. Main-stream capnography provides measurement of $CO_2$ concentrations directly from the patient airway (a few centimeters from the patient's mouth), when at this same point, an appropriate sensor is also placed to measure flow dynamics (generally using pressure drop, or thermal change measurements over a short passage in the airway). Since both the flow dynamic and $CO_2$ concentration measurements are practically instantaneous (when using non-dispersive IR spectroscopy), they are well synchronized and, hence, when calculating absolute $CO_2$ volume changes over exhalation time, a simple multiplication of both parameters provides a fairly accurate result. However, main-stream capnography suffers from the limitation that it is specifically defined for environments where there is a patient airway, i.e. for intubated patients, and is typically unsuitable for non-intubated patients.

In side-stream capnography, on the other hand, gas samples are collected from the breathing circuit, and the $CO_2$ sensor is located in a remote monitor. Side-stream capnography is thus applicable for both intubated patients as well as non-intubated patients monitored using, for example, breath sampling cannulas. However, as mentioned above, inherent to side-stream capnograph there is a delay, e.g., a system response time, between the flow changes and the $CO_2$ calculation and display. That is, even though the ventilator provokes a fast change in flow direction (pressure) and dynamics, when changing between the inhalation and exhalation stages of the created breath, the actual monitored and displayed $CO_2$ waveforms are delayed with respect to these changes in flow direction. This delay is the result of ventilator dead space volumes, sampling delay, delay due to the measuring, processing and displaying of the $CO_2$ waveform, and time lags caused by the physiological dead spaces. Such physiological deadspaces are generally non-homogenous. Accordingly, the air volumes contained in the physiological deadspaces change between patients having different anatomical spaces and/or health conditions. Even for a given patient and set-up, the dead space volumes change depending on alveolar recruitment and other physiological factors. Also, the transmit time of the sampled breath from the sampling inlet to the measurement cell may be influenced by several factors, which may change between patient and over time. These factors include pump stability, accumulation of liquids in the sampling line and filter, sampling line tolerances etc.

SUMMARY

The above effects render side-stream capnograph data desynchronized from flow dynamics measurements. Hence, side-stream capnography is typically not only a poor technological solution for providing volumetric capnography, but one that is typically not applicable for volumetric capnography. The present disclosure provides techniques to enable monitoring and measuring of changes in flow dynamics and $CO_2$ concentration measurements, while leveling out time delays related to the $CO_2$ sampling system.

Advantageously, the techniques disclosed herein enable accurate side-stream volumetric capnography by calculating the time lag of the $CO_2$ concentration measurement, such that an accurate synchronization in time between flow dynamics and $CO_2$ concentrations is achieved. This advantageously enables expanding volumetric capnography to non-intubated populations.

Furthermore, the techniques disclosed herein enable volumetric capnography when sampling is performed at the carina. In fact, sampling at the carina may further enhance the accuracy and/or sensitivity of the volumetric capnography and its ability to provide insights into the ventilation physiology, such as dead space breathing, shunt and $EtCO_2$ to $PaCO_2$ gradients, since performing the actual volumetric measurements at the carina removes a major part of the anatomical dead space and airway tubing dead space, leaving mainly those volumes that can change and that are indicative of the patient's respiratory condition.

According to some embodiments, there is provided a method for determining a volume of exhaled $CO_2$ as a function of time using side-stream capnography, the method including: obtaining flow dynamics measurements of a subject from a flow sensor; obtaining $CO_2$ concentration measurements of the subject from a side-stream $CO_2$ monitor; determining a duration of time ($\Delta T_{sl}$) for a sample of gas to flow from a reference point to the side-stream $CO_2$ monitor; synchronizing in time the $CO_2$ concentration measurement with the flow dynamics measurement, based on the determined $\Delta T_{sl}$; and determining a volume of $CO_2$ exhaled as a function of time, based on the flow dynamics measurement and the synchronized $CO_2$ concentration measurement.

According to some embodiments, the determining of the $\Delta T_{sl}$ may be performed based on an on-start of inhalation ($T_i$) a duration of time between $T_i$ until the capnograph depicts a deflection in the $CO_2$ concentration measurements ($\Delta T_{TOTAL}$) and a time required to wash away a gas volume encompassed between a Y-piece of a ventilator and the RP ($\Delta T_{FLUSH}$).

According to some embodiments, the $\Delta T_i$ may be derived from the flow dynamics measurements.

According to some embodiments, the $\Delta T_{FLUSH}$ may be calculated based on the inspiratory flow rate of the ventilator and the gas volume encompassed between the Y-piece of the ventilator and the RP.

According to some embodiments, the $\Delta T_{sl}$ may be calculated based on a difference in $\Delta T_{TOTAL}$ obtained when supplying the volume of air at at least two different flow rates.

According to some embodiments, the method may include providing a bolus of clean air or a bolus of air having known $CO_2$ concentration. According to some embodiments, the bolus of clean air may be provided at initiation of inhalation ($T_i$).

According to some embodiments, determining the $\Delta T_{sl}$ may include determining a time until a notch in the $CO_2$ concentration measurements, resulting from the bolus of clean air, is observed, and $T_i$ may determined based on the flow dynamics measurements.

According to some embodiments, determining the $\Delta T_{sl}$ may include determining a time until a $CO_2$ concentration measurement, corresponding to the known concentration of the provided bolus, is observed, wherein the known $CO_2$ concentration may include a concentration above a $CO_2$ concentration possibly observed in exhaled breath.

According to some embodiments, the method may include determining an undistorted shape of a $CO_2$ waveform by applying a shape distortion factor thereon. According to some embodiments, the $CO_2$ waveform may be derived from the $CO_2$ concentration measurements, and the shape distortion factor may be calculated based on a shape of a notch in the $CO_2$ waveform resulting from the provided bolus of air.

According to some embodiments, the method may include displaying the volume of $CO_2$ exhaled as a function of time on a display.

According to some embodiments, the method may be executed by a specially constructed processing unit, such as a capnography monitor or multi-purpose monitor, or it may be executed by a general purpose computer specifically configured by a computer program stored in the computer.

According to some embodiments, there is provided a device configured to determine a volume of exhaled $CO_2$ as a function of time, the device including: a side-stream $CO_2$ monitor configured to measure $CO_2$ concentration over time; and a processor. According to some embodiments, the processor may be configured to: obtain flow dynamics measurements; obtain the $CO_2$ concentration measurements from the side-stream $CO_2$ monitor; determine a duration of time ($\Delta T_{sl}$) for a sample of gas to flow from a reference point to the side-stream $CO_2$ monitor; synchronize in time the $CO_2$ concentration measurement with the flow dynamics measurement based on the determined $\Delta T_{sl}$; and determine a volume of $CO_2$ exhaled as a function of time based on the flow dynamics measurement and the synchronized $CO_2$ concentration measurement.

According to some embodiments, the device may include a flow sensor configured to provide flow dynamics measurements.

According to some embodiments, the processor may be configured to determine the $\Delta T_{sl}$ based on an inspiratory time ($\Delta T_{in}$) and a time to wash away a gas volume encompassed between a Y-piece of a ventilator and the RP ($\Delta T_{FLUSH}$).

According to some embodiments, the processor may be configured to calculate the $\Delta T_{in}$ based on a volume of air supplied by the ventilator and an inspiratory flow rate of the ventilator.

According to some embodiments, the processor may be configured to calculate the $\Delta T_{FLUSH}$ based on the inspiratory flow rate of the ventilator and the gas volume encompassed between the Y-piece of the ventilator and the RP.

According to some embodiments, the processor may be configured to calculate the $\Delta T_{FLUSH}$ based on a difference in $\Delta T_{in}$ obtained when supplying the volume of air at at least two different flow rates.

According to some embodiments, the device may be configured to provide a bolus of clean air or a bolus of air having a known $CO_2$ concentration. According to some embodiments, the device may include a tubing through which the bolus of air having a known $CO_2$ concentration may be supplied.

According to some embodiments, the bolus of clean air may be provided at initiation of inhalation ($T_i$). According to some embodiments, the processor may be configured to determine the $\Delta T_{sl}$ based on the bolus of clean air and based on a time until a notch in the $CO_2$ concentration measurements, resulting from the bolus of clean air, is observed. According to some embodiments, the $T_i$ may be determined based on the flow dynamics measurements.

According to some embodiments, the device may include a valve. According to some embodiments, the processor may be configured to control the operation of a valve. According to some embodiments, opening of the valve provides the bolus of clean air.

According to some embodiments, controlling the operation of the valve may include opening the valve such the said notch in the $CO_2$ concentration measurements will occur during a plateau in the $CO_2$ concentration measurements.

According to some embodiments, the processor may be configured to determine the $\Delta T_{sl}$ based on the bolus of air having a known $CO_2$ concentration and to determine a time until a $CO_2$ concentration measurement, corresponding to the known concentration of the provided bolus, is observed. According to some embodiments, the known $CO_2$ concentration may be a concentration above a $CO_2$ concentration possibly observed in exhaled breath.

According to some embodiments, the device may include a valve. According to some embodiments, the processor may be further configured to control the operation of a valve. According to some embodiments, opening of the valve may trigger the supply of the bolus of air having a known $CO_2$ concentration.

According to some embodiments, the device may be configured to determine an undistorted shape of a $CO_2$ waveform by applying a shape distortion factor thereon.

According to some embodiments, the $CO_2$ waveform may be derived from the $CO_2$ concentration measurements, and the shape distortion factor may be calculated based on a shape of a notch in the $CO_2$ waveform resulting from the provided bolus of air.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
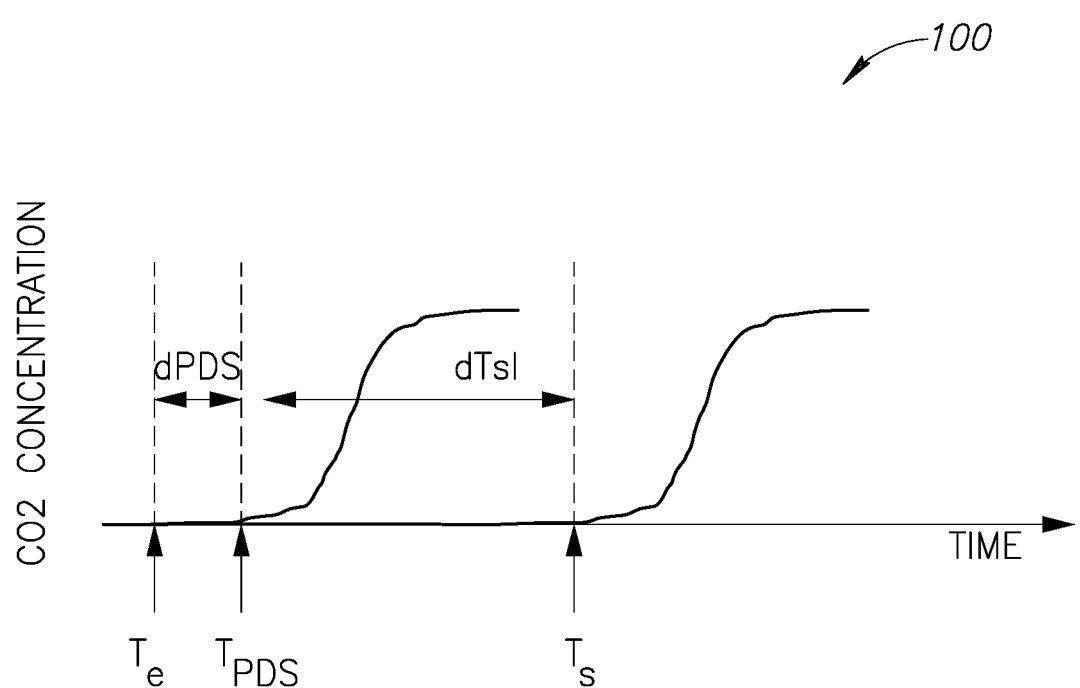
FIG. 1 shows an illustrative graph depicting time delays in $CO_2$ concentration measurements.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. Additionally, it is to be explicitly understood that any combination of any one or more of the disclosed embodiments may be applicable and is within the scope of the disclosure.

Unless specifically stated otherwise, as apparent from the following discussions, it is appreciated that throughout the specification discussions utilizing terms such as "processing", "computing", "calculating", "determining", or the like, refer to the action and/or processes of an electronic processing system, such as a medical monitor, a computer or computing system, or similar electronic computing device, that manipulates and/or transforms data represented as physical, such as electronic or electrical, quantities within the computing system's registers and/or memories into other data similarly represented as physical quantities within the computing system's memories, registers or other such information storage, transmission or display devices.

Embodiments of the present techniques may include apparatus configured to perform the operations herein. Such apparatus may be specially constructed for the desired purposes, such as capnography monitors or multi-purpose monitors, or it may include a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of non-transitory memory media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present techniques are not described with reference to any particular programming language. It will be appreciated that a variety of programming languages may be used to implement the teachings of the inventions as described herein.

The present disclosure generally relates to systems, devices and methods for side-stream volumetric capnography, including synchronizing $CO_2$ concentration measurements to breath flow dynamics measurements.

As used herein, the terms "patient" and "subject" may be interchangeably used and may refer to any subject undergoing breath monitoring, specifically subjects monitored using side-stream capnography.

As used herein, the terms "breath inhalation initiation time" and "$T_i$" may be used interchangeably and may refer to the point in time when a flow of breath changes direction from exhalation to inhalation. As used herein the terms "breath exhalation initiation time" and "$T_e$" may be used interchangeably and may refer to the point in time when a flow of breath changes direction from inhalation to exhalation. Because of the inherent characteristics of gas flow dynamics and measurement techniques, these points in time may be detected virtually instantaneously along the entire patient airway.

As used herein, the terms "measurement delay" and "$\Delta T_{sl}$" may refer to the duration for any sample of gas to traverse (flow) from a reference point (RP—e.g. an airway adapter sampling input) to the capnograph. As explained herein, $\Delta T_{sl}$ may be of inter- and/or intra-patient variability.

As used herein, the terms "reference point" and "RP" may refer to a point in the patient airway at which a synchronized $CO_2$ concentration is determined. According to some embodiments, the RP may be an airway adapter sampling input. According to some embodiments, the RP may be positioned within a double lumen endotracheal tube.

As used herein, the terms "synchronized $CO_2$ measurements" and "$CO_2$-RP" may be used interchangeably and may refer to $CO_2$ values as a function of time matched in time as if they were measured directly at the RP (devoid of sampling delay).

As used herein, the term "$\Delta T_{PDS}$" (where PDS stands for physiological dead space) may refer to the time required to clean the physiological dead space from the previously inhaled clean air and to start seeing the $CO_2$ exhaled by the patient. That is, the term may refer to the delay from exhalation initiation ($T_e$—defined above) to an initial increase in $CO_2$-RP (as defined above) measurements, which is due to the patient's physiological dead space.

As used herein, the term "$\Delta T_{FLUSH}$" may refer to the time to wash away gases present in mechanical dead space (from the previous exhalation) i.e. the airway volume encompassed between the ventilator Y-piece and the RP.

As used herein, the terms "inspiratory time" and "$\Delta T_{in}$" may refer to the time period during which a ventilator provides a volume of air to a ventilated patient. The inspiratory time may be calculated from the volume of air ($V_T$) provided to the patient and the inspiratory flow rate of the ventilator. As used herein, the terms "expiratory time" and "$\Delta T_{exp}$" may refer to the time period during which a ventilator removes air from the ventilated patient.

As used herein, the terms "volume of exhaled $CO_2$" and "$VCO_2$" may refer to the volume of $CO_2$ exhaled as a function of time, relative to the time points $T_i$ and $T_e$, and may be obtained by multiplying the flow dynamic signals and the time-matched $CO_{2-RP}$ signals.

As used herein, the terms "physiological dead space" and "PDS" may be used interchangeably and refer to the volume of air, which is inhaled but that does not take part in the gas exchange, because it remains in the conducting airways (anatomical dead space), or because it reaches alveoli that are not perfused or poorly perfused (alveolar dead space).

As used herein, the term "anatomical dead space" is that portion of the airways (such as the mouth and trachea to the bronchioles) that conducts gas to the alveoli. No gas exchange is possible in these spaces. The normal value for dead space volume (in mL) averages about a third of the resting tidal volume (450-500 mL). According to some embodiments, the terms "physiological dead space" and "anatomical dead space" may be used interchangeably.

According to one aspect of the disclosure, there is provided a device and method for determining a volume of exhaled $CO_2$ as a function of time using side-stream capnography.

According to some embodiments, the method may include obtaining flow dynamics measurements of a subject from a flow sensor; obtaining $CO_2$ concentration measurements of the subject from a side-stream $CO_2$ monitor; determining a duration of time ($\Delta T_{sl}$) required for a sample of gas to flow from a reference point to the side-stream $CO_2$ monitor; synchronizing in time the $CO_2$ concentration measurement with the flow dynamics measurement, based on the determined $\Delta T_{sl}$; and determining a volume of exhaled $CO_2$ as a function of time, based on the flow dynamics measurement and the synchronized $CO_2$ concentration measurement.

According to some embodiments, the $\Delta T_{sl}$ may be determined based on the on-start of inhalation (Ti), which can be extracted from the flow measurements, and a time to wash away a gas volume ($\Delta T_{FLUSH}$) encompassed between a ventilator output (e.g. a ventilator Y-piece) and the RP. According to some embodiments, the $\Delta T_{FLUSH}$ may be calculated based on the inspiratory flow rate of the ventilator and the gas volume encompassed between the Y-piece of the ventilator and the RP or between the endotracheal tube and the RP. The RP can also be moved closer to the patient and even be positioned within the patient's trachea at the carina. Thus, since the method obviates the need for placing the $CO_2$ sensor at the sampling input, it advantageously enables volumetric capnography in conjunction with endotracheal sampling using a double lumen endotracheal tube.

This embodiment is based upon the different characteristics of the exhalation stage and the inhalation stage. Quantification of the time that spans between the onset of exhalation ($T_e$) and the first detection of $CO_2$ at the RP, i.e. the calculation of $\Delta T_{sl}$, has some difficulties. As mentioned hereinabove, on exhalation, the volume of clean air that is removed from the physiological dead space, and the duration of this removal, is an unknown, which may depend upon many parameters, changing between patients as well as changing during patient respiratory fluctuations. The onset of the time delay resulting from the transport of the sample from the sampling point to the monitor is thus unknown. The difficulty of assessing $\Delta T_{sl}$ is further aggravated by the fact that not only is the $CO_2$ waveform delayed by a varying amount of time, but it also has a gradual increase, which makes it difficult to define and calculate the time between on-start of exhalation and $CO_2$ concentration build up at the RP.

In the inhalation stage, on the other hand, the air volume (also referred to as the mechanical dead space volume) encompassed between the ventilator output (e.g., the ventilator Y-piece) and the RP, which is driven back to the patient in order to refresh the patient with clean air, is a quasi-fixed volume. This, because it is a purely mechanical volume, unrelated to the patient's complex physiology and body shape. In addition, initiation of inhalation is followed by an abrupt decrease in the $CO_2$ concentration in the exhaled breath, manifested as a sharp decline in the $CO_2$ waveform. As a result, defining and calculating the time period between on-start of inhalation and a decrease in $CO_2$ concentration at the RP is considerably simpler.

Since the on-start of inhalation ($T_i$) is obtainable from the flow measurements, the time between $T_i$ until the capnograph depicts a deflection in the $CO_2$ concentration measurements (at the end of the $CO_2$ waveform) is known. Consequently, $\Delta T_{sl}$ can be calculated, since the total delay ($\Delta T_{TOTAL}$) equals the sum of $\Delta T_{FLUSH}$ and $\Delta T_{sl}$. The $\Delta T_{FLUSH}$ can be estimated from the deadspace volume (which is a fixed volume) and the flow dynamics.

It is further understood, that even though the volume of the Y-piece section is known and fixed, the actual time $\Delta T_{FLUSH}$ may not always be equal to multiplication of the flow rate and volume. This is because, during exhalation, there will usually be some exhaled breath that will diffuse past the Y-junction into the ventilator side. In other words, not all the exhaled air will channel only into the other side of the Y-junction used for removal. Hence, when inhalation starts, the wash out of the exhaled breath from the Y-piece to the sampling port of the airway will also include wash out of this diffused breath. However, since the level of diffused breath will be relative to the ventilator parameters, a correction can be included as a function of flow rate to correct for these discrepancies. Additionally or alternatively, the Y-piece can be designed such as to reduce to a minimum these affects, e.g. by adding a partial one-way valve at the Y-piece entrance to the ventilator side. According to some embodiments, the method further includes displaying the volume of exhaled $CO_2$ as a function of time, on a display.

According to another aspect of the disclosure, there is provided a system, device and method for determining a volume of exhaled $CO_2$ as a function of time using side-stream capnography. According to some embodiments, the method may include obtaining flow dynamics measurements of a subject from a flow sensor; obtaining $CO_2$ concentration measurements of the subject from a side-stream $CO_2$ monitor; determining a duration of time ($\Delta T_{sl}$) for a sample of gas to flow from a reference point to the side-stream $CO_2$ monitor; synchronizing in time the $CO_2$ concentration measurement with the flow dynamics measurement, based on the determined $\Delta T_{sl}$; and determining a volume of exhaled $CO_2$ as a function of time, based on the flow dynamics measurement and the synchronized $CO_2$ concentration measurement.

According to some embodiments, determining of the $\Delta T_{sl}$ may be performed based on an on-start of inhalation ($T_i$), and a duration of time between $T_i$ until the capnograph depicts a deflection in the $CO_2$ concentration measurements ($\Delta T_{TOTAL}$) (at the end of the $CO_2$ waveform). According to some embodiments, the $\Delta T_i$ may be derived from the flow dynamics measurements. According to some embodiments, the $\Delta T_{sl}$ may be calculated based on a difference in the total delay, $\Delta T_{TOTAL}$ obtained when supplying the volume of air at at least two different flow rates.

This embodiment takes into consideration that additional elements may be incorporated into the sampling line (e.g. between the Y piece and the sampling port). This is, for example, the case where Heat and Moisture Exchangers (HMEs) are used to create a humid and warm gas stream for the patient. The HME may be placed between the sampling airway adapter and the Y-piece, such that the large volume and filter of the HME does not interfere with the breath sampling rise time. As a result, the air volume (the mechanical deadspace volume) encompassed between the Y-piece and the RP is unknown.

In order to overcome the issue of varying volumes in the patient airway design, a technique disclosed herein suggests sampling air at two different sampling rates with a calibrated sampling flow rate ratio "k" between them. As a non-limiting example, the first sampling flow rate may be the conventional sampling flow rate of 50 ml/min, and the second sampling flow rate may be 25 ml/min or 100 ml/min, e.g., with ratios "k" 0.5 and 2 respectively.

Based on the different known sampling flow rates, the $\Delta T_{sl}$ may be calculated based on the below equations:

$$\Delta T1_{TOTAL} = \Delta T_{flush} + \Delta T_{sl}, \text{ and}$$

$$\Delta T2_{TOTAL} = \Delta T_{flush} + \Delta T_{sl} * k$$

According to some embodiments, the two flow rates may be achieved by adding a two-way solenoid valve to the capnograph close to the absorption cell where, in either or both paths, a different restrictor is incorporated. Hence, in the conventional mode, the restrictor is chosen to provide, for example, 50 ml/min, but when the solenoid is activated, and the direction of flow changes and passes past the second restrictor, the flow is changed accordingly. Since it is only the difference in restrictor that changes the flow rate, and both passive restrictors are not anticipated to change over time (like pumps, or sampling lines or filters filling with liquids), a calibration, such as at the factory, can be made to measure accurately the ratio "k", which is then stored in the memory, where "k" may remain constant over the life span even if the pump efficiency changes, since "k" is relative. According to some embodiments, the ratio "k" may change as a function of ambient temperature and pressure. Accordingly, according to some embodiments, the method may include adjusting "k" based on ambient pressure or temperature measurements. It is understood that the periodical changes in the sampling flow rate would not disturb continuous operation of the capnograph since, at both flow rates, the capnograph will retain its accuracy.

Advantageously, the method obviates the need for placing the $CO_2$ sensor at the sampling input and thus enables volumetric capnography in conjunction with endotracheal sampling using a double lumen endotracheal tube.

According to some embodiments, the method further includes displaying the volume of exhaled $CO_2$ as a function of time on a display.

According to yet another aspect, there is provided a system, device and method for determining a volume of exhaled $CO_2$ as a function of time using side-stream capnography. According to some embodiments, the method may include obtaining flow dynamics measurements of a subject from a flow sensor; obtaining $CO_2$ concentration measurements of the subject from a side-stream $CO_2$ monitor; determining a duration of time ($\Delta T_{sl}$) for a sample of gas to flow from a reference point to the side-stream $CO_2$ monitor; synchronizing in time the $CO_2$ concentration measurement with the flow dynamics measurement, based on the determined $\Delta T_{sl}$; and determining a volume of exhaled $CO_2$ as a function of time, based on the flow dynamics measurement and the synchronized $CO_2$ concentration measurement.

According to some embodiments, the $\Delta T_{sl}$ may be determined by providing a bolus of clean air at initiation of inhalation ($T_i$) and determining a time required until a notch in the $CO_2$ concentration measurements, resulting from the bolus of clean air, is observed.

As used herein, the term clean air may refer to ambient air or a gas used for oxygen supply. According to some embodiments, the clean air may be substantially devoid of $CO_2$. According to some embodiments, the term "substantially devoid" may refer to a gas containing only residual and/or trace amounts of $CO_2$. According to some embodiments, the clean air may have a $CO_2$ concentration of below 0.1%, below 0.05% or below 0.04%. Each possibility is a separate embodiment. According to some embodiments, the clean air may be the gas supplied by the ventilator.

According to some embodiments, the $T_i$ may be determined based on the flow dynamics measurements. This embodiment is designed to bypass the ventilator airway paths and hence remove the flushing region out of the equation. Advantageously, this embodiment is thus also applicable for non-intubated patients, for example subjects undergoing breath monitoring using a breath sampling cannula. Advantageously, the method also enables volumetric capnography in conjunction with endotracheal sampling using a double lumen endotracheal tube.

According to some embodiments, the capnograph, the tubing connected thereto and/or the ventilator may include an additional tube through which the bolus of clean air is supplied. According to some embodiments, the additional tube may be connected on one side to a position close to the sampling airway adapter inlet and on the other side to an appropriate position on the ventilator airway input section where there is always clean air. According to some embodiments, the additional tube may be configured to supply the clean air originating from the ventilator to the sampling airway adaptor (the RP). According to some embodiments, the additional tube may be connected on one side close to the inlet of a sampling tube and on the other side to a supply of clean air.

According to some embodiments, a valve system may be incorporated into the sampling system, such as on the side close to the sampling airway adapter inlet. According to some embodiments, the valve may be normally closed, preventing clean air being pumped in. According to some embodiments, the valve may be closed when the capnograph is in measurement mode.

According to some embodiments, the valve may be opened for a short period of time. According to some embodiments, the opening of the valve may be coordinated with the flow dynamics measurements, such that the opening of the valve is triggered by a change in direction from exhalation to inhalation. According to some embodiments, the operation of the valve and hence the injection of the bolus of clean air may be defined using algorithms, which, based on learned characteristics as well as measured patient respiration characteristics, enable triggering the injection at times so as to occur during the plateau of the $CO_2$ waveform. According to some embodiments, the valve control mechanism may induce a plurality of injections at predefined time intervals, such that at least one of the injections will occur when the $CO_2$ is at its plateau, creating a noticeable notch whose timing can be measured from the signal trigger.

According to some embodiments, the operation of the valve may be controlled by the capnograph. According to some embodiments, the opening of the valve may be controlled by the ventilator, such that the ventilator change from exhalation to inhalation will trigger opening of the valve. According to some embodiments, the opening of the valve may be controlled mechanically by the change in the flow pressure.

According to some embodiments, when the valve opens, a small bolus of clean air may be injected into the sampling line input region. Consequently, the clean air dilutes the exhaled air then being sampled. This since, as mentioned above, even when the flow changes from exhalation to inhalation, it is still the exhaled breath which is being sampled, e.g., the $CO_2$ waveform will still be at its plateau. According to some embodiments, the bolus of clean air then travels down the sampling line towards the capnograph, until reaching the sampling cell and consequently being displayed on the capnograph monitor.

According to some embodiments, the bolus of clean air may be synchronized with the on start of inhalation (e.g. ventilator inhalation), and the appearance of the sudden decrease (notch) in $CO_2$ concentration may facilitate the measuring of ΔTsl. According to some embodiments, when the injection of the bolus is synchronized with inhalation start, its position will be slightly before the abrupt fall in $CO_2$, depictive of the start in inhalation and will be observed as a notch preceding the fall.

According to some embodiments, in order to ensure the accuracy of the measurement, the position of the valve relative to the sampling line may be of a same order of distance as the airway adapter sampling inlets to the T-junction that connects the valve with the sampling line.

According to some embodiments, the valve may be configured to ensure that the pressure drop created by the flow direction of the bolus of clean air, when the valve is opened, is negligible, such that the capnograph flow rate characteristics are prevented from being substantially changed as a result thereof According to some embodiments, the volume of the bolus of clean air may be large enough to ensure that a recognizable notch in the $CO_2$ concentration is created prior to the descent in $CO_2$ concentration (resulting from inhalation), while simultaneously ensuring that the accuracy of the $CO_2$ concentration measurements is not compromised. According to some embodiments, the entry time of the bolus of clean air may be long enough to ensure that a recognizable notch in the $CO_2$ concentration is created prior to the descent in $CO_2$ concentration (resulting from inhalation), while simultaneously ensuring that the accuracy of the $CO_2$ concentration measurements is not compromised According to some embodiments, the entry time of the bolus of clean air may be in the range of 50 msec-1 sec, 100 msec-600 msec or 200 msec-500 msec, for example.

According to some embodiments, the valve may be a solenoid valve, a check valve, a shut-off valve, a butterfly valve, a ball valve, a diaphragm, a pinch valve or any other suitable valve. Each possibility is a separate embodiment. According to some embodiments, the valve may be controlled electronically, by pressure or mechanically or any other suitable control mechanism. Each possibility is a separate embodiment. According to some embodiments, the operation of the valve may be controlled by the capnograph, by the ventilator, by an external processor, manually or any combination thereof.

According to some embodiments, a signal may be received from the capnograph, the ventilator, or an external processor recommending manually operation of the valve (e.g. open the valve). Additionally or alternatively, the valve may be manually operated according to a user protocol. According to some embodiments, manually triggering (e.g. opening) the valve may induce a signal to the capnograph that the valve has been opened, consequently triggering the measurement of the time durations of travel. According to some embodiments, manual triggering of the valve may induce subsequent, optionally automatic, sequential pulsatile openings of the valve so as to ensure timing with the plateau of the $CO_2$ concentration. According to some embodiments, the capnograph, the ventilator, or the external processor may be configured to calculate the entry time of the bolus of clean air based on the opening of the valve.

According to some embodiments, the $\Delta T_{sl}$ may be assessed periodically in order to improve accuracy. According to some embodiments, the periodic assessment may be performed according to a predetermined schedule. Alternatively, the $\Delta T_{sl}$ may be assessed based on identified changes in the breathing pattern (e.g. changes in flow dynamic).

According to some embodiments, providing the bolus of clean air further enables to correct the spatial distribution of the obtained $CO_2$ waveform (representing the $CO_2$ concentration over time as calculated from the $CO_2$ concentration measurements). When a gas samples flows through the sample tube, the part of the sample flowing closer to the walls of the sampling tube are slowed down due to the friction of the sampling tube's wall. The part of the sample flowing in the sampling tube's center therefore reaches the sampling cell prior to the part of the sample flowing along the sampling tube's wall. As a result, the waveform obtained when using breath sampling tubes as in side-stream capnography is spread out relative to the waveform obtained when using an in-line $CO_2$ sensor connected directly to the airway, as in main-stream capnography. The degree of spreading depends on the length of the sampling tube, on the incorporation of additional elements along the sampling line, such as, but not limited to, filters, and the like. By providing a bolus of clean air, the distortion in the spatial distribution of the waveform can be measured and thus corrected for. This since the duration, and thus the volume over time, of the bolus provided is known, and based upon that the anticipated shape of the notch can be determined. The deviation between the shape of the obtained notch and the anticipated shape can subsequently serve as a transform and/or correction factor (also referred to herein as a shape distortion factor), which can be applied on the waveform obtained from the patient, so as to correct for the distortion in its shape. According to some embodiments, the method includes displaying the volume of exhaled $CO_2$ as a function of time on a display and/or the undistorted $CO_2$ waveform on a display.

According to yet another aspect, there is provided a system, device and method for determining a volume of exhaled $CO_2$ as a function of time using side-stream capnography, the method including obtaining flow dynamics measurements of a subject from a flow sensor; obtaining $CO_2$ concentration measurements of the subject from a side-stream $CO_2$ monitor; determining a duration of time ($\Delta T_{sl}$) for a sample of gas to flow from a reference point to the side-stream $CO_2$ monitor; synchronizing in time the $CO_2$ concentration measurement with the flow dynamics measurement, based on the determined $\Delta T_{sl}$; and determining a volume of exhaled $CO_2$ as a function of time, based on the flow dynamics measurement and the synchronized $CO_2$ concentration measurements.

According to some embodiments, the $\Delta T_{sl}$ may be determined by providing a bolus of air having a known $CO_2$ concentration and determining the time until a $CO_2$ concentration measurement, corresponding to the known concentration, is observed. According to some embodiments, the known $CO_2$ concentration may include a concentration higher than a $CO_2$ concentration potentially observed in exhaled breath. The abnormally high $CO_2$ concentration can then be identified as a peak in the $CO_2$ concentration measurements. According to some embodiments, the known $CO_2$ concentration may include a concentration lower than a $CO_2$ concentration observed in exhaled breath. The abnormally low $CO_2$ concentration can then be identified as a notch in the $CO_2$ concentration measurements.

According to some embodiments, the $T_i$ may be determined based on the flow dynamics measurements. As above, this embodiment is designed to bypass the ventilator airway paths and hence remove the flushing region out of the equation. Advantageously, this embodiment is thus also applicable for non-intubated patients, for example subjects undergoing breath monitoring using a breath sampling cannula. Advantageously, the method also enables volumetric capnography in conjunction with endotracheal sampling using a double lumen endotracheal tube.

According to some embodiments, the capnograph, the tubing connected thereto and/or the ventilator may include an additional tube through which the air having the known $CO_2$ concentration is supplied. According to some embodiments, the additional tube may be connected on one side to a position close to the sampling airway adapter inlet and on the other side to an appropriate gas supply. According to some embodiments, the additional tube may be connected on one side close to the inlet of a sampling tube and on the other side to a supply of air having the known $CO_2$ concentration. According to some embodiments, the additional tube may be configured to supply the air having the known $CO_2$ concentration, such as, but not limited to, room air, to the sampling airway adaptor (the RP).

As above, time for an injected bolus of gas to travel from the sample line to the capnograph is utilized for calculating $\Delta T_{sl}$. However, according to this embodiment, the calculation is based on the known concentration of $CO_2$ in the injected gas. According to some embodiments, the air injected may be supplied from any gas source and may be injected into the sampling line, for example, by utilizing a valve.

According to some embodiments, the triggering of the valve may be synchronized in time with the onset of the inhalation. Alternatively, the triggering of the valve may not have to be synchronized in time with the onset of the inhalation and may, for example, be provoked by the capnograph periodically whenever it feels that new measurements are necessary. As a non-limiting example, if the capnograph measures and monitors its own flow rate, the capnograph may provoke a new measurement of $\Delta T_{sl}$ whenever the capnograph itself detects a change in its own flow rate by more than a predefined level. This predefined level is based upon a known accuracy level or resolution as required, or as such one that would affect the final volumetric calculation.

According to some embodiments, the bolus of air having the known $CO_2$ concentration may be synchronized with the on start of inhalation (e.g. ventilator inhalation), and the appearance of the sudden decrease or increase (notch or peak) in $CO_2$ concentration may facilitate the measuring of $\Delta T_{sl}$. According to some embodiments, when the injection of the bolus is synchronized with inhalation start, its position will be slightly before the abrupt fall in $CO_2$, depictive of the start in inhalation and will be observed as a notch or a peak preceding the fall.

According to some embodiments, the operation of the valve and hence the injection of the bolus of air having the known $CO_2$ concentration, may be defined using algorithms, which, based on learned characteristics as well as measured patient respiration characteristics, enable triggering the injection at times so as to occur during the plateau of the $CO_2$ waveform. According to some embodiments, the valve control mechanism may induce a plurality of injections at predefined time intervals, such that at least one of the injections will occur when the $CO_2$ is at its plateau, creating a noticeable notch whose timing can be measured from the signal trigger.

According to some embodiments, the operation of the valve, and hence the injection of the bolus of air having the known $CO_2$ concentration, may occur at any point of the breath cycle (i.e. at any point on the $CO_2$ waveform).

According to some embodiments, the valve may be a solenoid valve, a check valve, a shut-off valve, a butterfly valve, a ball valve, a diaphragm, a pinch valve or any other suitable valve. According to some embodiments, the valve may be controlled electronically, by pressure or mechanically or any other suitable control mechanism. According to some embodiments, the operation of the valve may be controlled by the capnograph, by the ventilator, by an external processor, manually or any combination thereof.

According to some embodiments, manual operation of the valve may be made because of a recommendation received from the capnograph, because of a recommendation received from ventilator, according to a user protocol or any combination thereof. According to some embodiments, manually triggering (e.g. opening) the valve may induce a signal to the capnograph that the valve has been opened, consequently triggering the measurement of the time durations of travel. According to some embodiments, manual triggering of the valve may induce subsequent, optionally automatic, sequential pulsatile openings of the valve so as to ensure timing with the plateau of the $CO_2$ concentration.

According to some embodiments, providing the bolus of clean air further enables to correct the spatial distribution of the obtained waveform (representing the $CO_2$ concentration over time as calculated from the $CO_2$ concentration measurements). When a gas sample flows through the sample tube, the part of the sample flowing in the sampling tube's center reaches the sampling cell prior to the part of the sample flowing along the sampling tube's wall, due to the friction caused by the wall material. As a result, the waveform obtained when using breath sampling tubes as in side-stream capnography is distorted (spread out) relative to the waveform obtained when using an in-line $CO_2$ sensor connected directly to the patient airway, as in main-stream capnography. The degree of spreading depends on the length of the sampling tube, on the incorporation of additional elements along the sampling line, such as, but not limited to, filters and the like. By providing a bolus of clean air, the distortion in the spatial distribution of the waveform can be measured and thus corrected for. This since the duration, and thus the volume over time of the bolus provided, is known, and based upon that the anticipated shape of the notch can be determined. The deviation between the shape of the obtained notch and the anticipated shape can subsequently serve as a transforming and/or correction factor (also referred to herein as a shape distortion factor), which can be applied on the waveform obtained from the patient, so as to correct for the distortion in its shape.

According to yet another aspect of the disclosure there is provided a method and device for determining an undistorted shape of a $CO_2$ waveform. The method may include obtaining $CO_2$ concentration measurements from a side-stream capnograph, deriving $CO_2$ waveforms therefrom and reefing the shape of the $CO_2$ waveforms by applying a shape distortion factor thereon. According to some embodiments, the shape distortion factor may be determined by providing a bolus of clean air (or air having a known $CO_2$ concentration, as essentially described herein), determining the shape of a notch in the $CO_2$ waveform resulting from the provided bolus of gas and determining the deviation of the determined shape from that anticipated. That is, since the volume over time of the provided bolus is known, the degree of distortion of its flow through the sampling tube, caused by the friction exerted by the sampling tube's wall, may be determined.

Reference is now made to FIG. 1, which shows an illustrative graph 100 depicting the time delays in $CO_2$ concentration measurements. After the onset of exhalation $T_e$, there will be a first time lag, $\Delta T_{PDS}$, preceding the increase in $CO_2$ at the sampling site. This time lag is due to the time required to promote cleaning of the physiological dead space from previously inhaled air, which has remained in the conducting airways, and thus not taken part in the gas exchange. At $T_{PDS}$ "real" exhalation, i.e. air that takes part in the gas exchange, is commenced. However, a second time lag, $\Delta T_{sl}$, is incurred to the time necessary for the gas sample to traverse (flow) from the reference point (RP) to it being sensed and calculated by the capnograph. The $T_e$ will therefore be measured only at $T_S$, i.e. at a total time delay of $\Delta T_{PDS}+\Delta T_{sl}$ and at a time delay of $\Delta T_{sl}$ from the actual increase in $CO_2$ in the exhaled breath. The measured $CO_2$ waveform is thus shifted (dotted line) relative to flow dynamics measurements.

Figure 2:
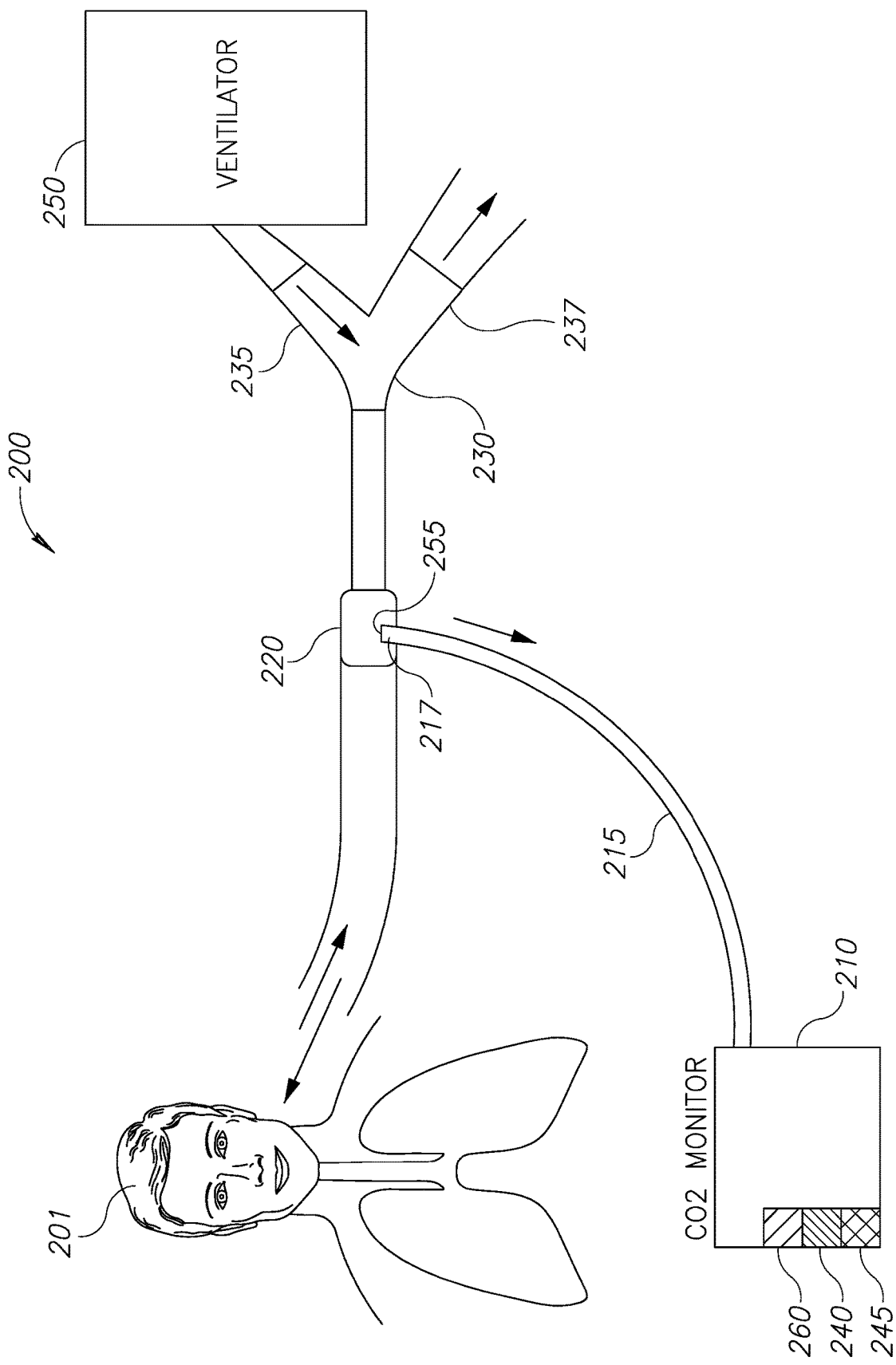
FIG. 2 schematically illustrates a system configured to determine a volume of exhaled $CO_2$ as a function of time using side-stream capnography, according to some embodiments.

Reference is now made to FIG. 2, which schematically illustrates a system 200 for determining a volume of exhaled $CO_2$ as a function of time using side-stream capnography. System 200 includes a ventilator 250 connected to a patient 201 through an airway adaptor 220. Exiting airway adaptor 220 is a breath sampling tube 215 configured to allow breath samples being drawn from airway adapter 220 for measurement by side-stream $CO_2$ monitor 210 (e.g. a capnograph). System 200 further includes a processor 230 here depicted as an integral part of side-stream $CO_2$ monitor 210, however other options, such as, for example, an external processor, are also applicable and thus within the scope of the disclosure. Processor 230 is configured to obtaining flow dynamics measurements from a flow sensor 240 and $CO_2$ concentration measurements form a $CO_2$ sensor 260 (e.g. a Nondispersive Infrared (NDIR) $CO_2$ Sensor). Flow sensor 240 may, as here depicted, be an integral part of side-stream $CO_2$ monitor 210, however other configurations, (e.g. a separate flow sensor) are also applicable and as such within the scope of the present disclosure. Processor 230 is further configured to determine a duration of time ($\Delta T_{sl}$) for a sample of gas to flow from a reference point 225 in airway adapter 220 to side-stream $CO_2$ monitor 210, to synchronize in time the $CO_2$ concentration measurement with the flow dynamics measurement, based on the determined $\Delta T_{sl}$ and to determine a volume of exhaled $CO_2$ as a function of time, based on the obtained flow dynamics measurement and the synchronized $CO_2$ concentration measurement.

Processor 245 may determine the $\Delta T_{sl}$ based on the on-start of inhalation (Ti), extracted from the flow measurements, and on a time required to wash away a gas volume ($\Delta T_{FLUSH}$) encompassed between ventilator Y-piece 230 and airway adaptor 220. Optionally, the $\Delta T_{FLUSH}$ may be calculated based on the inspiratory flow rate of the ventilator and the fixed gas volume encompassed between Y-piece 230 and airway adaptor 220.

It is understood, that even though the volume of Y-piece 230 is known, the actual time $\Delta T_{FLUSH}$ may not always be equal to multiplication of the flow rate and volume. Thus, because during exhalation there may be some exhaled breath diffusing past Y-piece 230 into a ventilator side 235 of Y-piece 230, e.g., not all the exhaled air will channel into the exhaust side 237 of Y-piece 230 used for removal. Hence, when inhalation starts, the wash out of the exhaled breath from Y-piece 230 to a sampling inlet 217 of airway adapter 220 may also include wash out of this diffused breath. However, since the level of diffused breath will be relative to the parameters of ventilator 250, a correction can be included as a function of flow rate to correct for these discrepancies. Additionally or alternatively, Y-piece 230 can be designed such as to reduce to a minimum these affects, e.g. Y-piece 230 may include a partial one-way valve at an entrance into ventilator side 235 of Y-piece 230.

Figure 3:
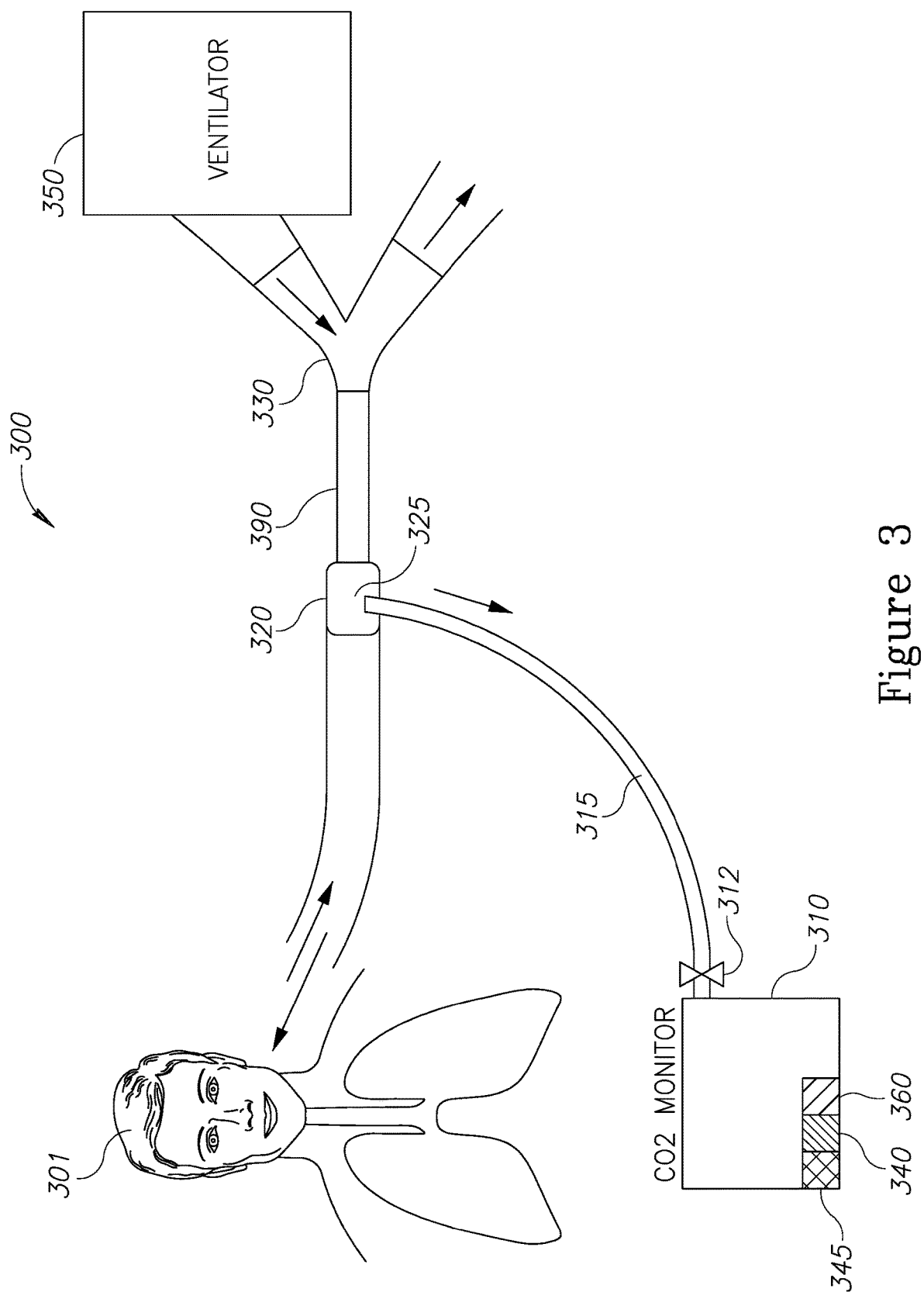
FIG. 3 schematically illustrates a system configured to determine a volume of exhaled $CO_2$ as a function of time using side-stream capnography, according to some embodiments.

Reference is now made to FIG. 3, which schematically illustrates a system 300 for determining a volume of exhaled $CO_2$ as a function of time using side-stream capnography. System 300 includes a ventilator 350, connected to a patient 301 through an airway adaptor 320, and a heat and moisture exchanger 390 positioned between airway adapter 320 and a Y-piece 330 of ventilator 350. Exiting airway adaptor 320 is a breath sampling tube 315 configured to allow breath samples being drawn from airway adapter 320 for measurement by side-stream $CO_2$ monitor 310 (e.g. a capnograph). System 300 further includes a processor 345 here depicted as an integral part of side-stream $CO_2$ monitor 210, however other options, such as for example an external processor is also applicable and thus within the scope of the disclosure.

Processor 345 is configured to obtain flow dynamics measurements from a flow sensor 340 and $CO_2$ concentration measurements form a $CO_2$ sensor 360 (e.g. a Nondispersive Infrared (NDIR) $CO_2$ Sensor). Flow sensor 340 may, as here depicted, be an integral part of side-stream $CO_2$ monitor 310, however other configurations, (e.g. a separate flow sensor) are also applicable and as such within the scope of the present disclosure. Processor 345 is further configured to determine a duration of time ($\Delta T_{sl}$) required for a sample of gas to flow from a reference point 325 in airway adapter 320 to side-stream $CO_2$ monitor 310, to synchronize in time the $CO_2$ concentration measurement with the flow dynamics measurement, based on the determined $\Delta T_{sl}$ and to determine a volume of exhaled $CO_2$ as a function of time, based on the obtained flow dynamics measurement and the synchronized $CO_2$ concentration measurement.

Processor 345 may determine the $\Delta T_{sl}$ based an on-start of inhalation ($T_i$), and a duration of time between $T_i$ until side-stream $CO_2$ monitor 310 depicts a deflection in the $CO_2$ concentration measurements ($\Delta T_{TOTAL}$) (at the end of the $CO_2$ waveform). $\Delta T_{sl}$ may then be calculated by processor 345 based on a difference in the total delay, $\Delta T_{TOTAL}$, obtained when supplying the volume of air at at least two different flow rates.

Due to the incorporation of heat and moisture exchangers 390, the air volume (the mechanical dead space volume) encompassed between Y-piece 330 and airway adapter 320 is unknown. However, based on the different known sampling flow rates, heat and moisture exchangers 390 may be taken out of the equation and $\Delta T_{sl}$ may be calculated, as described herein.

According to some embodiments, the different flow rates, may be achieved by adding a two-way solenoid valve 312 to side-stream $CO_2$ monitor 310 close to the absorption cell (not shown), where in either or both paths, a restrictor (not shown) is incorporated, such that when two-way solenoid valve 312 is activated, and the direction of flow changes and passes past the restrictor, the flow is changed accordingly. Since it is only the difference in the restrictor that changes the flow rate, and restrictors are not anticipated to change over time (as opposed to pumps, sampling lines or filters), a factory calibration can be made to measure accurately the ratio "k", which can then be stored in processor 345. The ratio "k" may change as function of ambient temperature and pressure. Processor 345 may therefore be configured to adjust "k" based on ambient pressure or temperature measurements.

Figure 4:
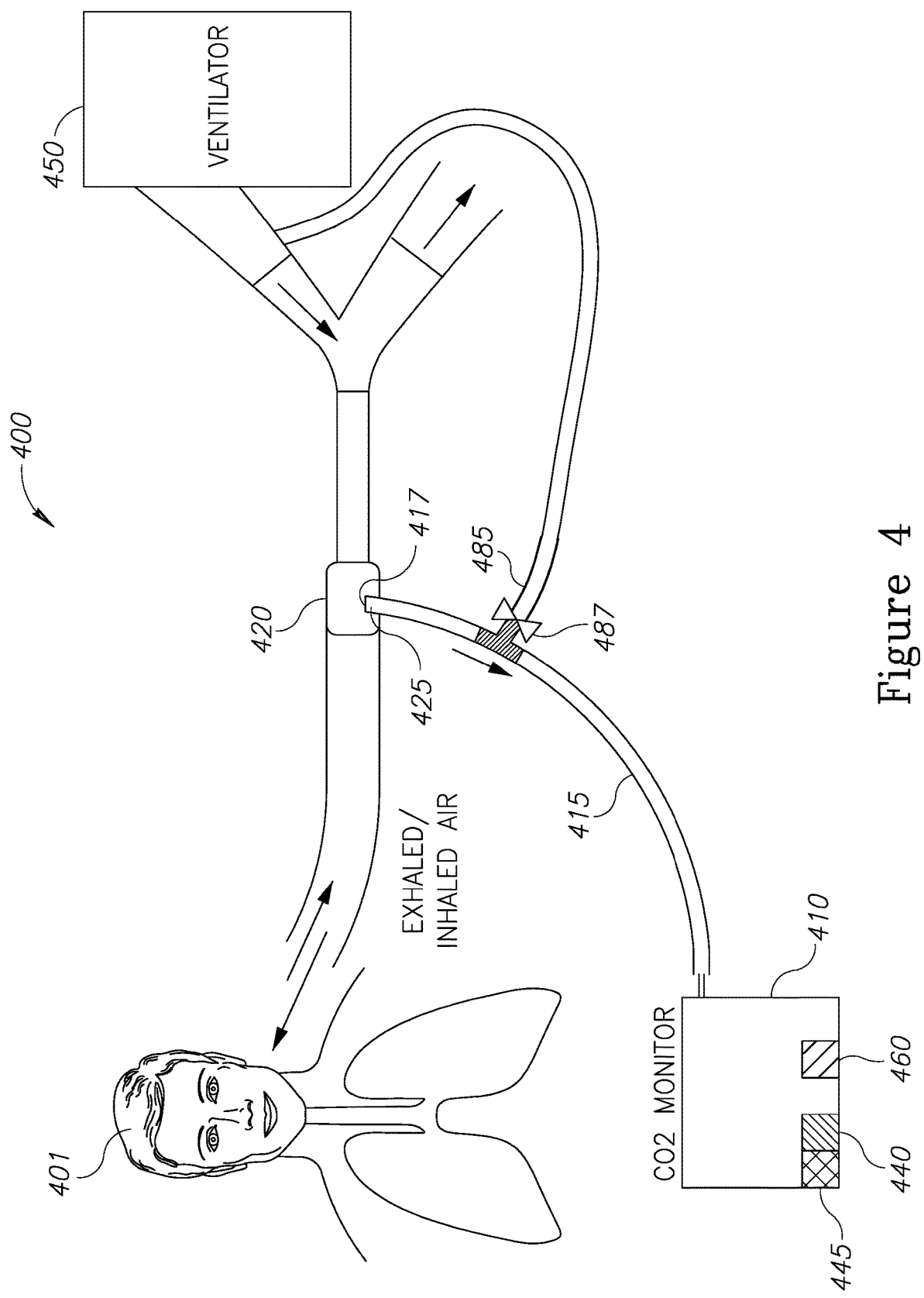
FIG. 4 schematically illustrates a system configured to determine a volume of exhaled $CO_2$ as a function of time using side-stream capnography, according to some embodiments.

Reference is now made to FIG. 4, which schematically illustrates a system 400 for determining a volume of exhaled $CO_2$ as a function of time using side-stream capnography. System 400 includes a ventilator 450 connected to a patient 401 through an airway adaptor 420. Exiting airway adaptor 420 is a breath sampling tube 415 configured to allow breath samples being drawn from airway adapter 420 for measurement by side-stream $CO_2$ monitor 410 (e.g. a capnograph). System 400 further includes a processor 445 here depicted as an integral part of side-stream $CO_2$ monitor 410, however other options, such as, for example, an external processor is also applicable and thus within the scope of the disclosure. Processor 445 is configured to obtain flow dynamics measurements from a flow sensor 440 and $CO_2$ concentration measurements from a $CO_2$ sensor 460 (e.g. a Nondispersive Infrared (NDIR) $CO_2$ Sensor). Flow sensor 440 may, as here depicted, be an integral part of side-stream $CO_2$ monitor 410, however other configurations, (e.g. a separate flow sensor) are also applicable and as such within the scope of the present disclosure. Processor 445 is further configured to determine a duration of time ($\Delta T_{sl}$) for a sample of gas to flow from a reference point 425 in airway adapter 420 to side-stream $CO_2$ monitor 410, to synchronize in time the $CO_2$ concentration measurement with the flow dynamics measurement, based on the determined $\Delta T_{sl}$ and to determine a volume of exhaled $CO_2$ as a function of time, based on the obtained flow dynamics measurement and the synchronized $CO_2$ concentration measurement.

Processor 445 may determine the $\Delta T_{sl}$ by providing a bolus of clean air at initiation of inhalation ($T_i$) and determining a time required until a notch in the $CO_2$ concentration measurements (and/or the $CO_2$ waveform derived therefrom), resulting from the bolus of clean air, is observed.

Processor 445 may further determine a shape distortion factor based on the shape of the notch in the $CO_2$ waveform and its deviation from an anticipated shape, as described herein. The shape distortion factor may subsequently be utilized by processor 445 to cancel out distortions to the shape of the $CO_2$ waveform caused by friction of the sampling tube's wall on breath sample flow therein, thereby enabling the determining of the "true" shape of the obtained $CO_2$ waveform.

To provide the bolus of clean air, system 400 includes a tube 485 through which the bolus of clean air is supplied. Tube 485 is connected on one side to a position close to sampling inlet 417 of airway adapter 420 and on the other side to ventilator 450. Tube 485 can thus supply the clean air originating from the ventilator to inlet 417.

Figure 7:
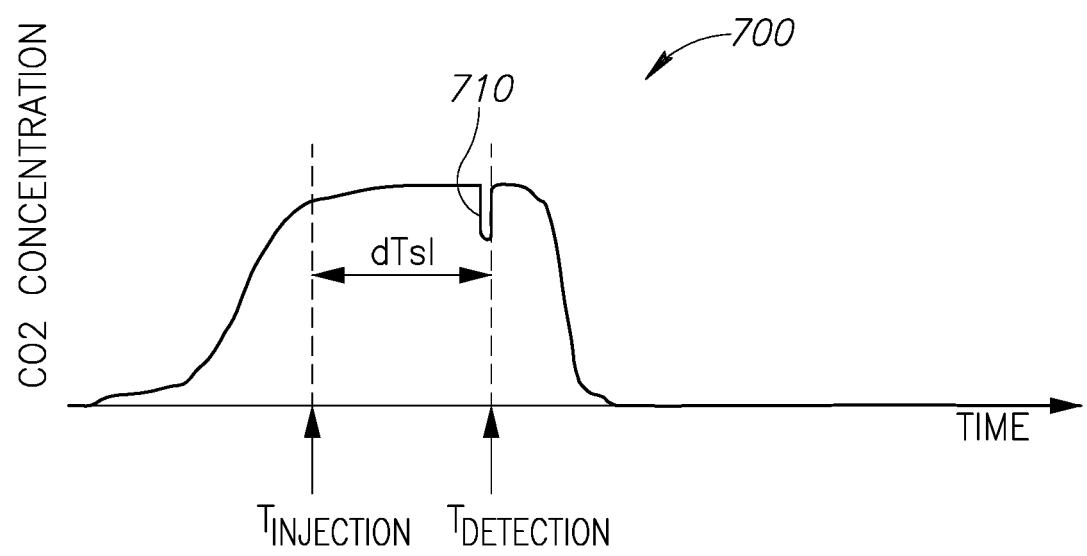
FIG. 7 schematically illustrates a capnogram with a notch in $CO_2$ concentration, according to some embodiments.

System 400 further includes a valve 487 positioned in proximity to inlet 417. Valve 487 may be normally closed, preventing clean air from being pumped in at all times. Valve 487 may be opened for a short period of time and the opening may, for example, be coordinated with the flow dynamics measurements, such that the opening of the valve is triggered by a change in direction from exhalation to inhalation. Additionally or alternatively, operation of valve 487 and hence the injection of the bolus of clean air, may be defined using algorithms, which, based on learned characteristics as well as measured patient respiration characteristics, enable triggering the injection so as to occur during the plateau of the $CO_2$ waveform. Additionally or alternatively, valve 487 may induce a plurality of injections at predefined time intervals, such that at least one of the injections will occur when the $CO_2$ is at its plateau, creating a noticeable notch whose timing can be measured from the signal trigger. Processor 430 may then be configured to determine $\Delta T_{sl}$ based on the time for the bolus of clean air to be measured by capnograph 410 and to create a notch in the $CO_2$ waveform, as depicted in FIG. 7.

Figure 5:
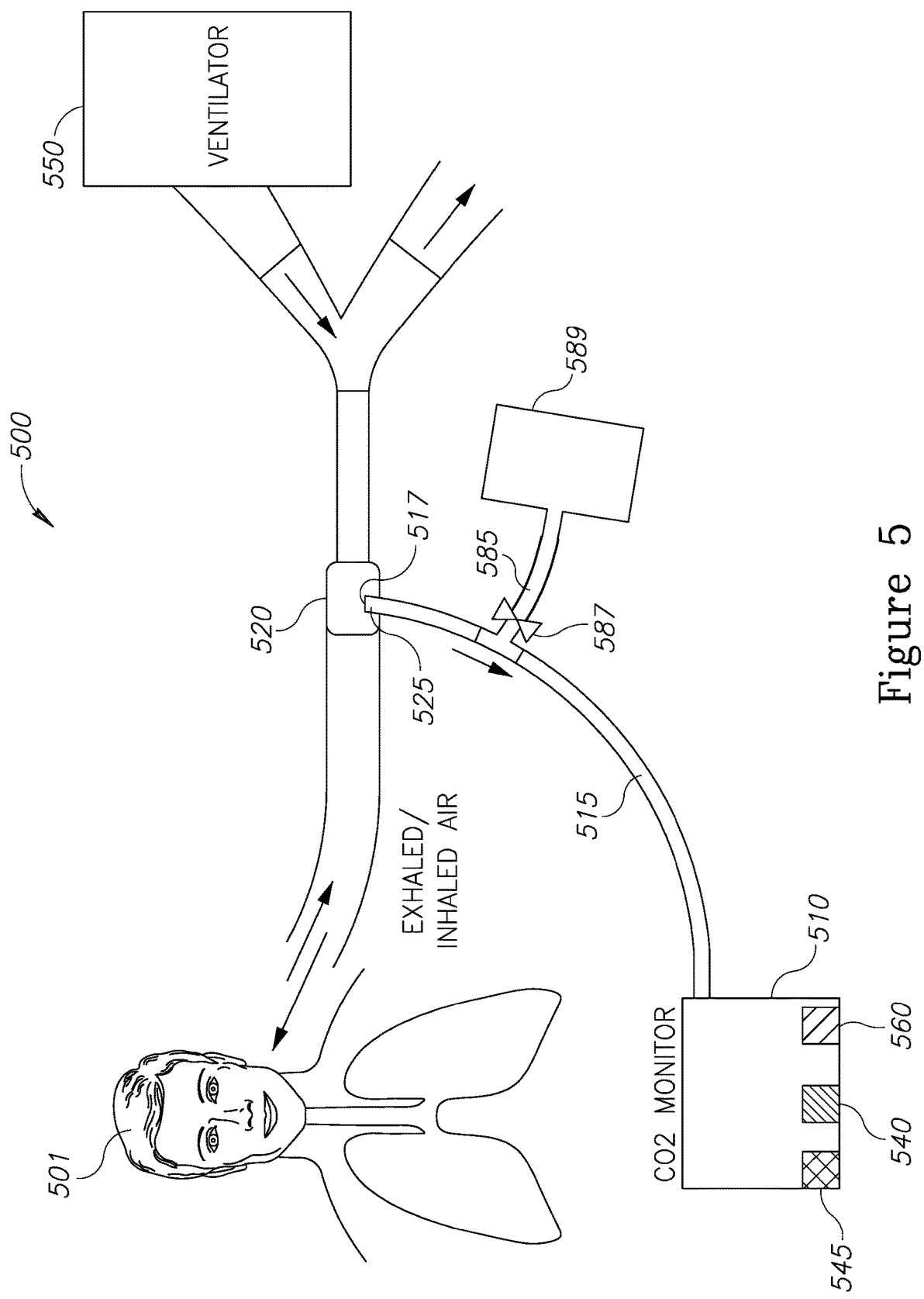
FIG. 5 schematically illustrates a system configured to determine a volume of exhaled $CO_2$ as a function of time using side-stream capnography, according to some embodiments.

Reference is now made to FIG. 5, which schematically illustrates a system 500 for determining a volume of exhaled $CO_2$ as a function of time using side-stream capnography. System 500 includes a ventilator 550 connected to a patient 501 through an airway adaptor 520. Exiting airway adaptor 520 is a breath sampling tube 515 configured to allow breath samples being drawn from airway adapter 520 for measurement by side-stream $CO_2$ monitor 510 (e.g. a capnograph). System 500 further includes a processor 545 here depicted as an integral part of side-stream $CO_2$ monitor 510, however other options, such as, for example, an external processor is also applicable and thus within the scope of the disclosure. Processor 545 is configured to obtaining flow dynamics measurements from a flow sensor 540 and $CO_2$ concentration measurements form a $CO_2$ sensor 560 (e.g. a Nondispersive Infrared (NDIR) $CO_2$ Sensor). Flow sensor 540 may, as here depicted, be an integral part of side-stream $CO_2$ monitor 510, however other configurations, (e.g. a separate flow sensor) are also applicable and as such within the scope of the present disclosure. Processor 545 is further configured to determine a duration of time ($\Delta T_{sl}$) for a sample of gas to flow from a reference point 525 in airway adapter 520 to side-stream $CO_2$ monitor 510, to synchronize in time the $CO_2$ concentration measurement with the flow dynamics measurement, based on the determined $\Delta T_{sl}$ and to determine a volume of exhaled $CO_2$ as a function of time, based on the obtained flow dynamics measurement and the synchronized $CO_2$ concentration measurement.

Processor 545 may determine the $\Delta T_{sl}$ by providing a bolus of air having a known $CO_2$ concentration and determining the time until a $CO_2$ concentration measurement, corresponding to the known concentration, is observed. The known $CO_2$ concentration may include a concentration higher than a $CO_2$ concentration potentially observed in exhaled breath, thus leading to a peak in the $CO_2$ concentration measurement. Alternatively, the known $CO_2$ concentration may include a concentration lower than a $CO_2$ concentration observed in exhaled breath, thus causing a notch in the $CO_2$ concentration measurement (and/or the $CO_2$ waveform derived therefrom).

Processor 545 may further determine a shape distortion factor based on the shape of the notch in the $CO_2$ waveform and its deviation from an anticipated shape, as described herein. The shape distortion factor may subsequently be utilized by processor 545 to cancel out distortions to the shape of the $CO_2$ waveform caused by friction of the sampling tube's wall on breath sample flow therein, thereby enabling the determining of the "true" shape of the obtained $CO_2$ waveform.

To provide the bolus of clean air, system 500 includes a tube 585 through which the bolus of clean air is supplied. Tube 585 is connected on one side to a position close to sampling inlet 517 of airway adapter 520 and on the other side to an air supply 589 configured to supply the bolus of air having the known $CO_2$ concentration.

System 500 further includes a valve 587 positioned in proximity to inlet 517. Valve 587 may be normally closed, preventing clean air from being pumped in at all times. Valve 587 may be opened for a short period of time and the opening may, for example, be coordinated with the flow dynamics measurements, such that the opening of the valve is triggered by a change in direction from exhalation to inhalation. Additionally or alternatively, operation of valve 587 and hence the injection of the bolus of air having the known $CO_2$ concentration may be defined using algorithms, which, based on learned characteristics as well as measured patient respiration characteristics, enable triggering the injection so as to occur during the plateau of the $CO_2$ waveform. Additionally or alternatively, valve 587 may induce a plurality of injections ensuring that the notch/peak is identifiable. Processor 545 may then be configured to determine $\Delta T_{sl}$ based on the time for the bolus of clean air to be measured by capnograph 510 and to create a notch in the $CO_2$ waveform, as depicted in FIG. 7.

Figure 6:
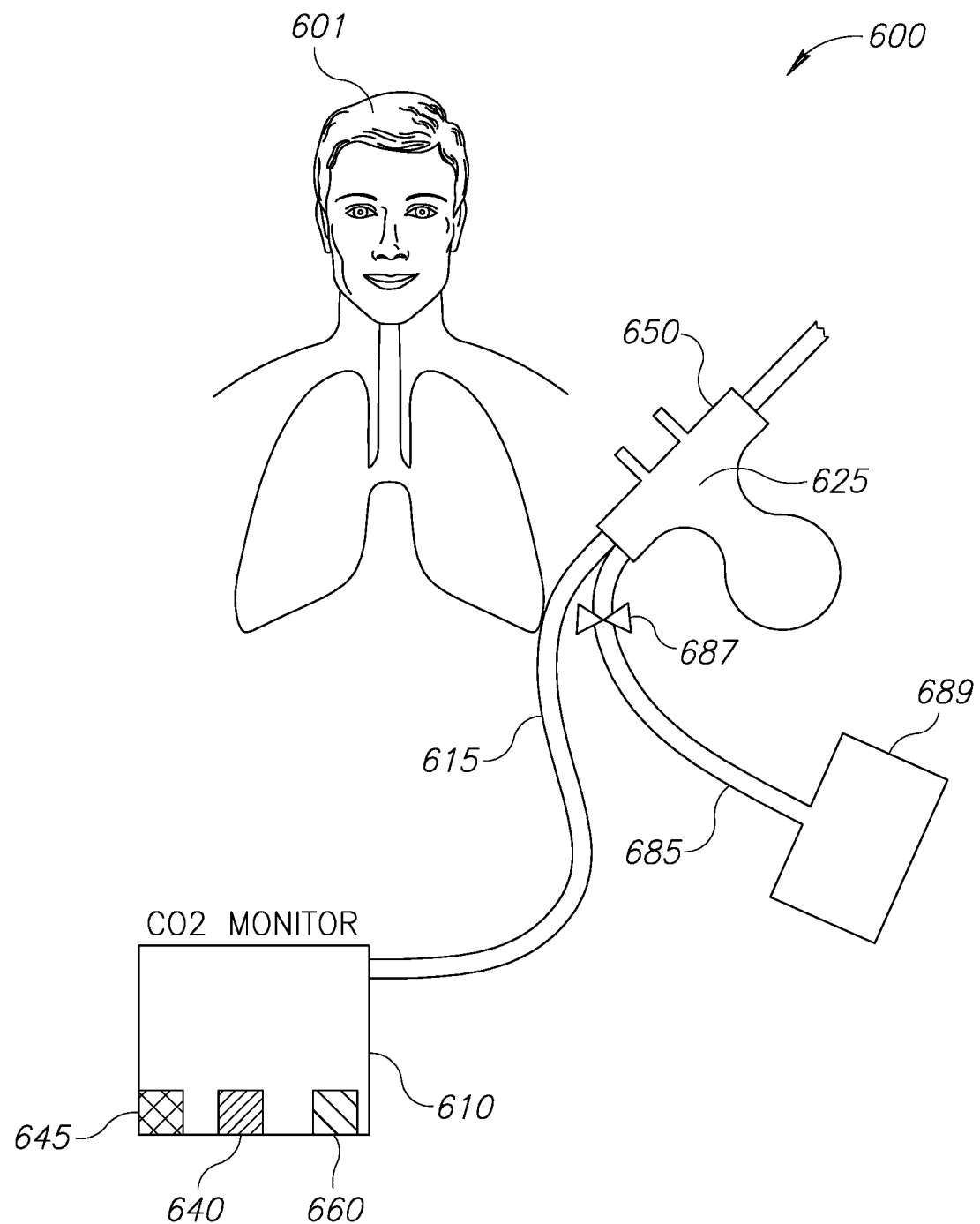
FIG. 6 schematically illustrates a system configured to determine a volume of exhaled $CO_2$ as a function of time using side-stream capnography, according to some embodiments.

Reference is now made to FIG. 6, which schematically illustrates a system 600 for determining a volume of exhaled $CO_2$ as a function of time using side-stream capnography. System 600 includes a gas sampling cannula 650 connected to a patient 601 and allowing breath samples to flow through sampling tube 615 for measurement by side-stream $CO_2$ monitor 610 (e.g. a capnograph). System 600 further includes a processor 645 here depicted as an integral part of side-stream $CO_2$ monitor 610, however other options, such as, for example, an external processor is also applicable and thus within the scope of the disclosure. Processor 645 is configured to obtaining flow dynamics measurements from a flow sensor 640 and $CO_2$ concentration measurements form a $CO_2$ sensor 660 (e.g. a Nondispersive Infrared (NDIR) $CO_2$ Sensor). Flow sensor 640 may, as here depicted, be an integral part of side-stream $CO_2$ monitor 610, however other configurations, (e.g. a separate flow sensor) are also applicable and as such within the scope of the present disclosure.

Processor 645 is further configured to determine a duration of time ($\Delta T_{sl}$) for a sample of gas to flow from a reference point 625 in gas sampling cannula 650 to side-stream $CO_2$ monitor 610, to synchronize in time the $CO_2$ concentration measurement with the flow dynamics measurement, based on the determined $\Delta T_{sl}$ and to determine a volume of exhaled $CO_2$ as a function of time, based on the obtained flow dynamics measurement and the synchronized $CO_2$ concentration measurement.

Processor 645 may determine the $\Delta T_{sl}$ by providing a bolus of air having a known $CO_2$ concentration and determining the time until a $CO_2$ concentration measurement, corresponding to the known concentration, is observed. The known $CO_2$ concentration may include a concentration higher than a $CO_2$ concentration potentially observed in exhaled breath, thus leading to a peak in the $CO_2$ concentration measurement. Alternatively, the known $CO_2$ concentration may include a concentration lower than a $CO_2$ concentration observed in exhaled breath, thus causing a notch in the $CO_2$ concentration measurement (and/or the $CO_2$ waveform derived therefrom).

Processor 645 may further determine a shape distortion factor based on the shape of the notch in the $CO_2$ waveform and its deviation from an anticipated shape, as described herein. The shape distortion factor may subsequently be utilized by processor 645 to cancel out distortions to the shape of the $CO_2$ waveform caused by friction of the sampling tube's wall on breath sample flow therein, thereby enabling the determining of the "true" shape of the obtained $CO_2$ waveform.

To provide the bolus of clean air, system 600 includes a tube 685 through which the bolus of clean air is supplied. Tube 685 is connected on one side to a position close to gas sampling cannula 650 and on the other side to an air supply 689 configured to supply the bolus of air having the known $CO_2$ concentration.

System 600 further includes a valve 687 positioned in proximity to patient gas sampling cannula 650. Valve 687 may be normally closed, preventing clean air from being pumped in at all times. Valve 687 may be opened for a short period of time and the opening may, for example, be coordinated with the flow dynamics measurements, such that the opening of the valve is triggered by a change in direction from exhalation to inhalation. Additionally or alternatively, operation of valve 687 and hence the injection of the bolus of air having the known $CO_2$ concentration may be defined using algorithms, which, based on learned characteristics as well as measured patient respiration characteristics, enable triggering the injection so as to occur during the plateau of the $CO_2$ waveform. Additionally or alternatively, valve 687 may induce a plurality of injections ensuring an identifiable notch/peak. Processor 645 may then be configured to determine $\Delta T_{sl}$ based on the time required for the bolus of clean air to be measured by capnograph 610 and to create a notch in the $CO_2$ waveform, as depicted in FIG. 7.

Reference is now made to FIG. 7, which shows an illustrative a capnogram 700, according to some embodiments. Capnogram 700 depicts the $CO_2$ concentration over time in a patient's exhaled breath. Capnogram 700 enables calculation of $\Delta T_{sl}$ based on an injection of a bolus of clean air and/or a bolus of air having a known $CO_2$ concentration into the patient's breath sample, at a predetermined time point ($T_{injection}$) during the patient's breath cycle. Due to the time for the bolus of air to travel from the reference point (e.g. within the airway adaptor) to the $CO_2$ monitor, the notch 710 (or peak) in the $CO_2$ concentration is only observed at $T_{detection}$, and the time-lag between $T_{injection}$ and $T_{detection}$ corresponds to $\Delta T_{sl}$.

Figure 8:
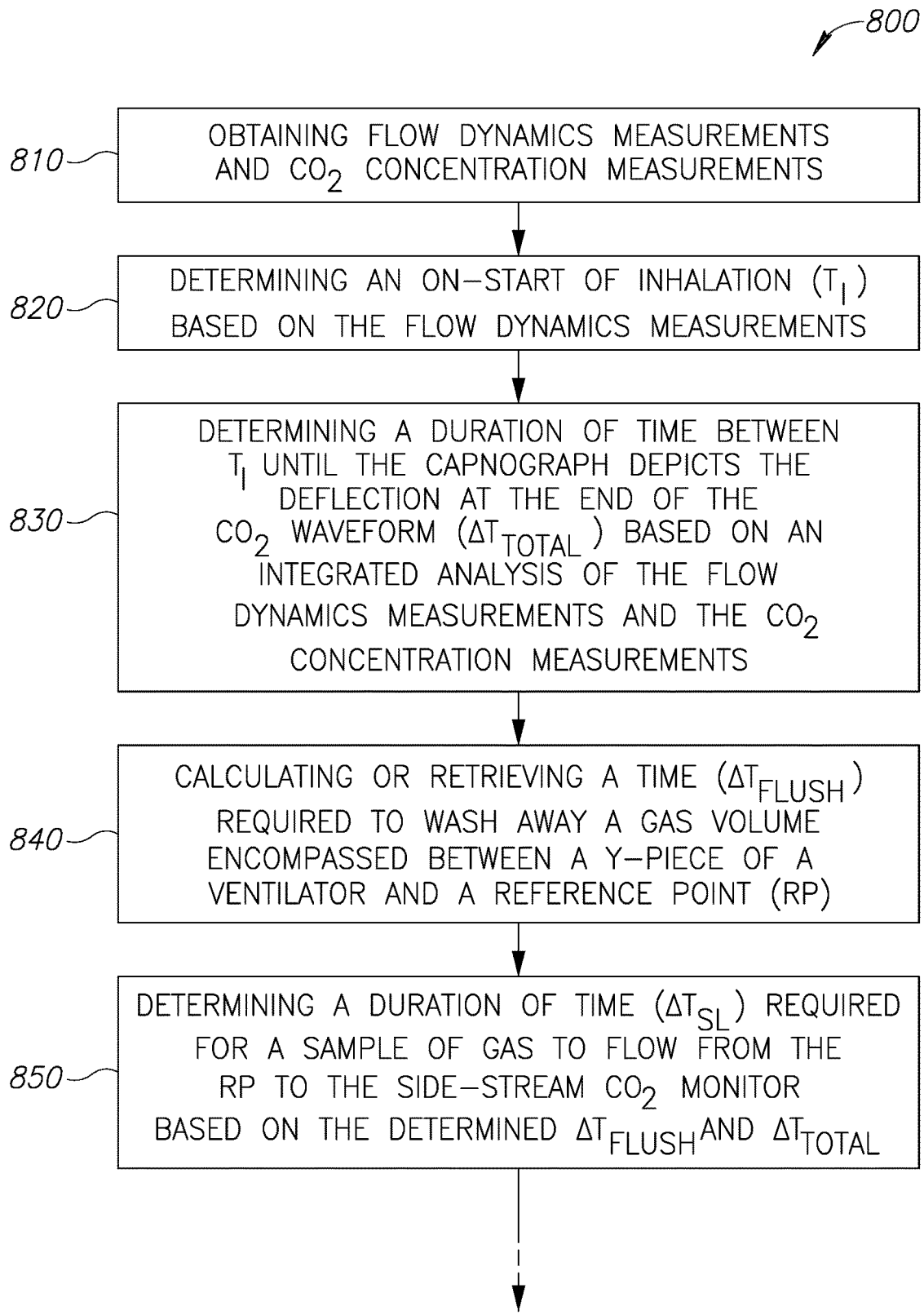
FIG. 8 is an illustrative flowchart of a method to perform volumetric side-stream capnograph, according to some embodiments.

Reference is now made to FIG. 8, which is an illustrative flowchart 800 of a method for performing volumetric sidestream capnography, according to some embodiments. It is understood that certain steps are sequential whereas other steps may be performed either sequentially or simultaneously with other steps of the method.

At step 810, flow dynamics measurements and $CO_2$ concentration measurements are obtained. At step 820 an on-start of inhalation ($T_i$) is determined based on the flow dynamics measurements. At step 830, the duration of time between $T_i$ until the capnograph depicts a deflection in the $CO_2$ concentration measurements ($\Delta T_{TOTAL}$) (at the end of the $CO_2$ waveform) is determined based on an integrated analysis of the flow dynamics measurements and the $CO_2$ concentration measurements. At step 840, a time to wash away a gas volume encompassed between a Y-piece of a ventilator and the RP ($\Delta T_{FLUSH}$) is calculated based on the inspiratory flow rate of the ventilator and the gas volume encompassed between the Y-piece of the ventilator and the RP. It is understood to one of ordinary skill in the art that $\Delta T_{FLUSH}$ may be predetermined and thus retrieved rather than being calculated as an integral part of the method. At step 850, a duration of time ($\Delta T_{sl}$) for a sample of gas to flow from a reference point to the side-stream $CO_2$ monitor is calculated based on the determined $\Delta T_{FLUSH}$ and $\Delta T_{TOTAL}$. At step 860, the $CO_2$ concentration measurement is synchronized in time with the flow dynamics measurement, based on the determined $\Delta T_{sl}$; and in step 870, the volume of $CO_2$ exhaled as a function of time is determined based on the flow dynamics measurement and the synchronized $CO_2$ concentration measurement.

Figure 9:
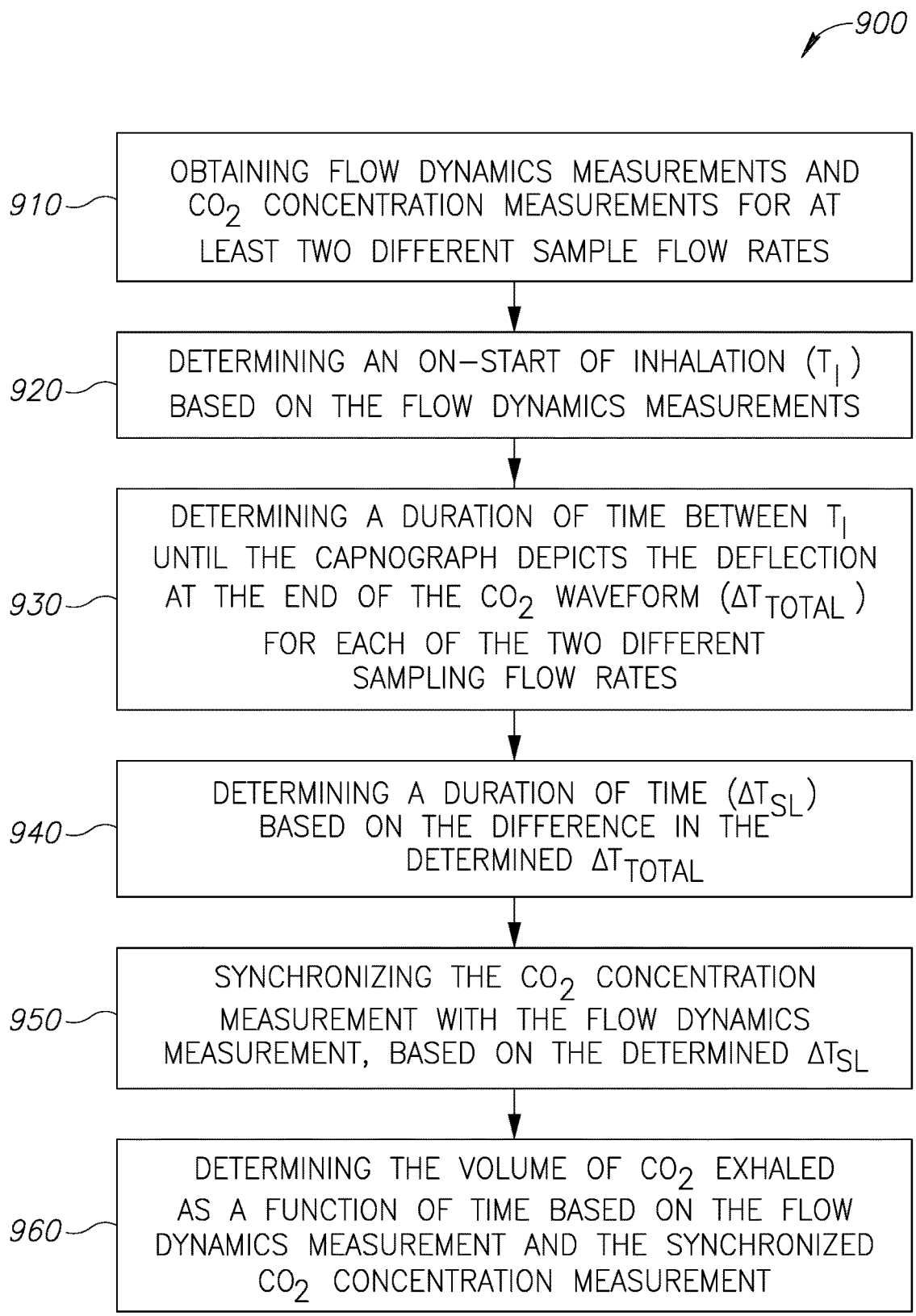
FIG. 9 is an illustrative flowchart of a method to perform volumetric side-stream capnograph, according to some embodiments.

Reference is now made to FIG. 9, which is an illustrative flowchart 900 of a method for performing volumetric sidestream capnography, according to some embodiments. It is understood that certain steps are sequential whereas other steps may be performed either sequentially or simultaneously with other steps of the method.

At step 910, flow dynamics measurements and $CO_2$ concentration measurements are obtained for at least two different sample flow rates. At step 920 an on-start of inhalation ($T_i$) is determined based on the flow dynamics measurements. At step 930, the duration of time between $T_i$ until the capnograph depicts a deflection in the $CO_2$ concentration measurements ($\Delta T_{TOTAL}$) (at the end of the $CO_2$ waveform) is determined for each of the two different sampling flow rates. At step 940, a duration of time ($\Delta T_{sl}$) for a sample of gas to flow from a reference point to the side-stream $CO_2$ monitor is calculated based on the difference in $\Delta T_{TOTAL}$ obtained. At step 950, the $CO_2$ concentration measurement is synchronized in time with the flow dynamics measurement, based on the determined $\Delta T_{sl}$; and in step 960, the volume of $CO_2$ exhaled as a function of time is determined based on the flow dynamics measurement and the synchronized $CO_2$ concentration measurement.

Figure 10:
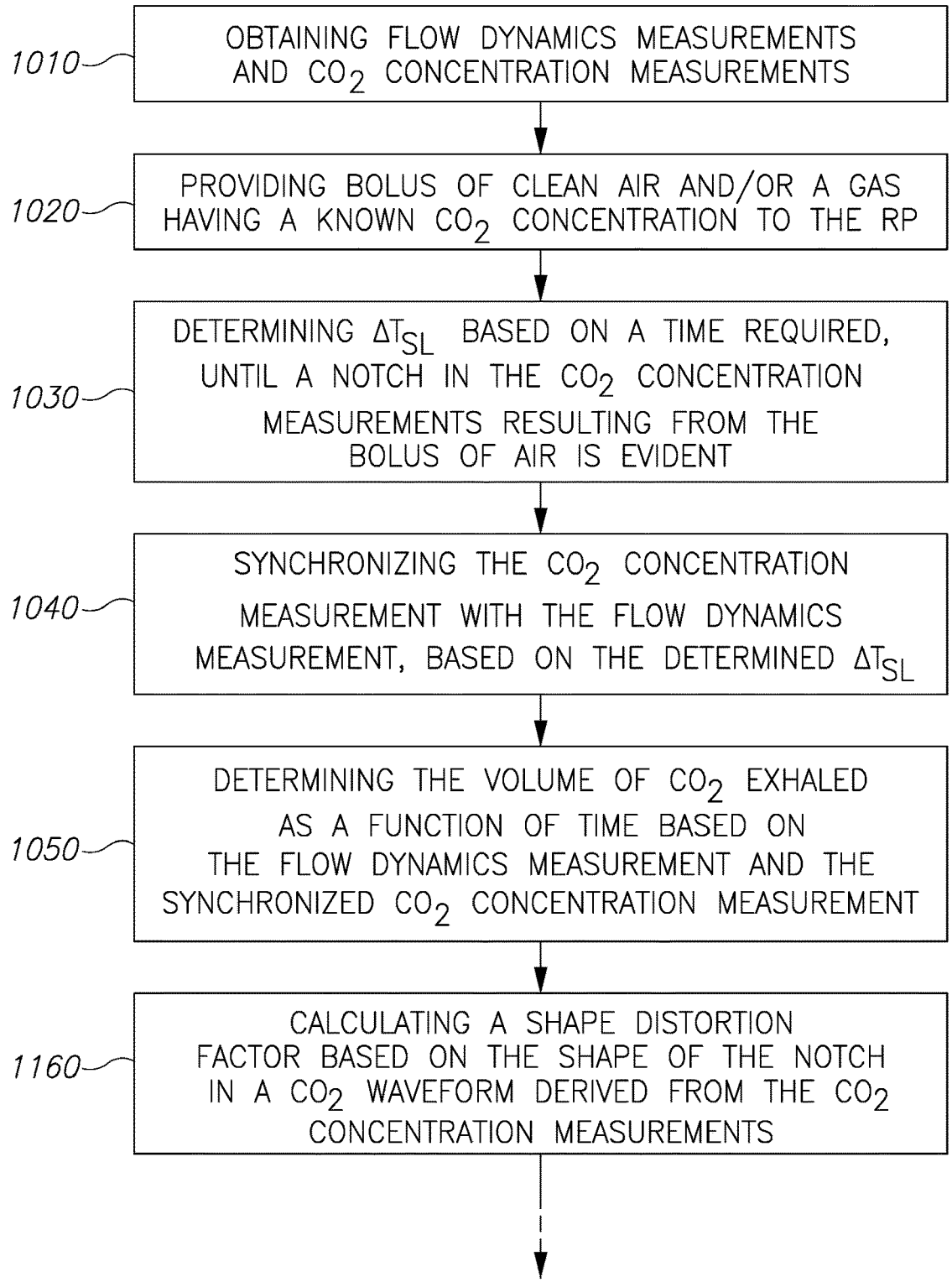
FIG. 10 is an illustrative flowchart of a method to perform volumetric side-stream capnograph, according to some embodiments.

Reference is now made to FIG. 10, which is an illustrative flowchart 1000 of a method for performing volumetric side-stream capnography, according to some embodiments. It is understood that certain steps are sequential whereas other steps may be performed either sequentially or simultaneously with other steps of the method.

At step 1010, flow dynamics measurements and $CO_2$ concentration measurements (and or $CO_2$ waveforms) are obtained. At step 1020 a bolus of clean air and/or a bolus of a gas having a known $CO_2$ concentration is provided. The bolus of air may be optionally be provided at initiation of inhalation ($T_i$), as further explained herein. This may be of particular importance when the air supplied is clean air from the ventilator. At step 1030 the duration of time ($\Delta T_{sl}$) for a sample of gas to flow from a reference point to the sidestream $CO_2$ monitor is calculated based on a time required, until a notch in the $CO_2$ concentration measurements, resulting from the bolus of supplied air, is evident. At step 1040, the $CO_2$ concentration measurement is synchronized in time with the flow dynamics measurement, based on the determined $\Delta T_{sl}$; and in step 1050, the volume of $CO_2$ exhaled as a function of time is determined based on the flow dynamics measurement and the synchronized $CO_2$ concentration measurement.

Figure 11:
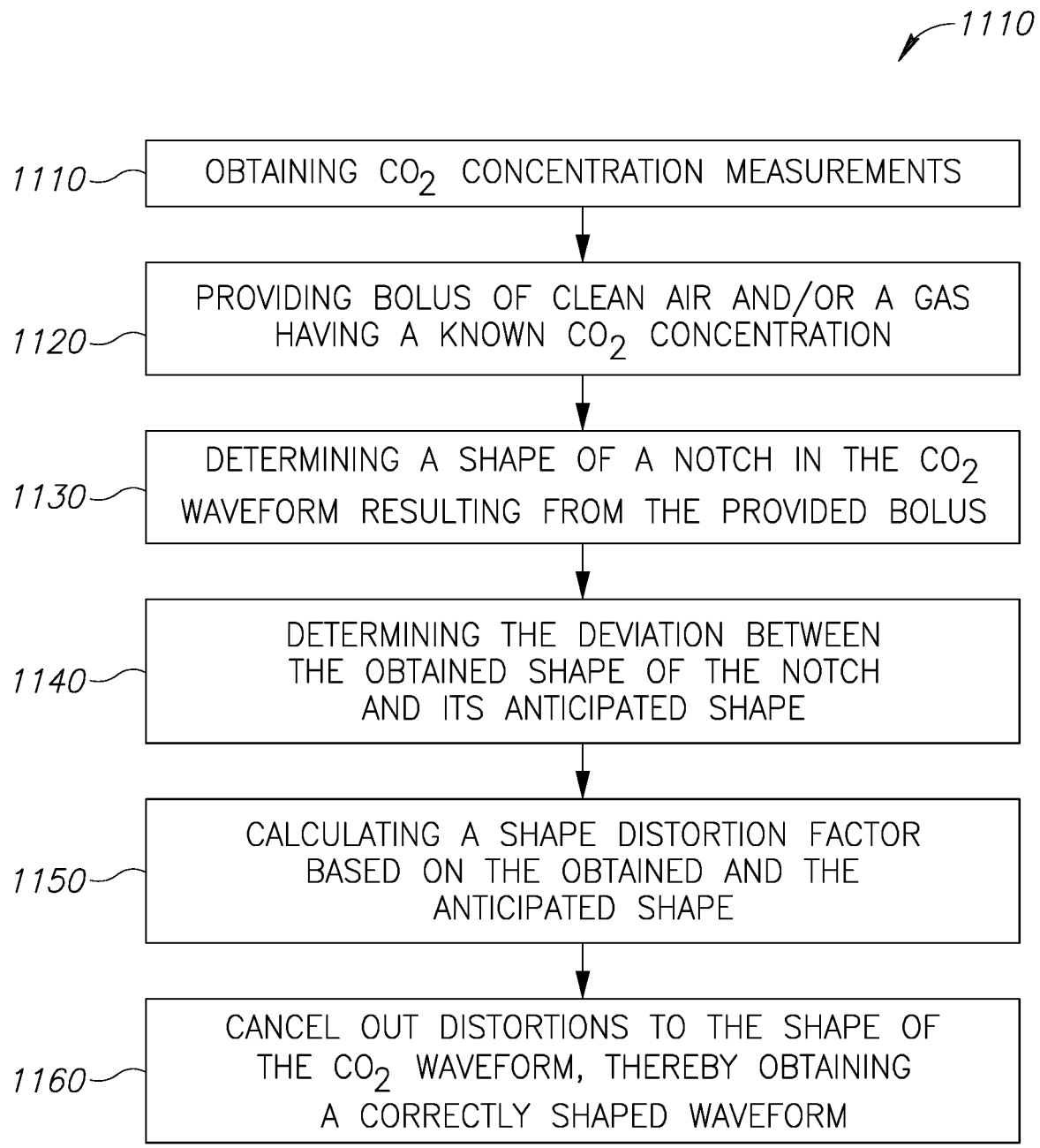
FIG. 11 is an illustrative flowchart of a method to determine an undistorted shape of a $CO_2$ waveform, according to some embodiments.

Reference is now made to FIG. 11, which is an illustrative flowchart 1100 of a method for determining an undistorted shape of a $CO_2$ waveform, according to some embodiments. It is understood that certain steps are sequential whereas other steps may be performed either sequentially or simultaneously with other steps of the method. At step 1110, $CO_2$ concentration measurements are obtained and a $CO_2$ waveform determined therefrom. In step 1120 a bolus of clean air and/or a bolus of a gas having a known $CO_2$ concentration is provided, and in 1130 the shape of a notch in the $CO_2$ waveform resulting from the provided bolus of gas is determined. In step 1140, the anticipated shape of the notch is determined based on its known volume over time, as described herein. In step 1150 a shape distortion factor is calculated based on the deviation between the obtained shape of the notch and its anticipated shape. In step 1160, the calculated shape distortion factor is applied on the $CO_2$ waveform, so as to correct for the distortion in its shape, thereby obtaining a $CO_2$ waveform having an undistorted shape.

Figure 12:
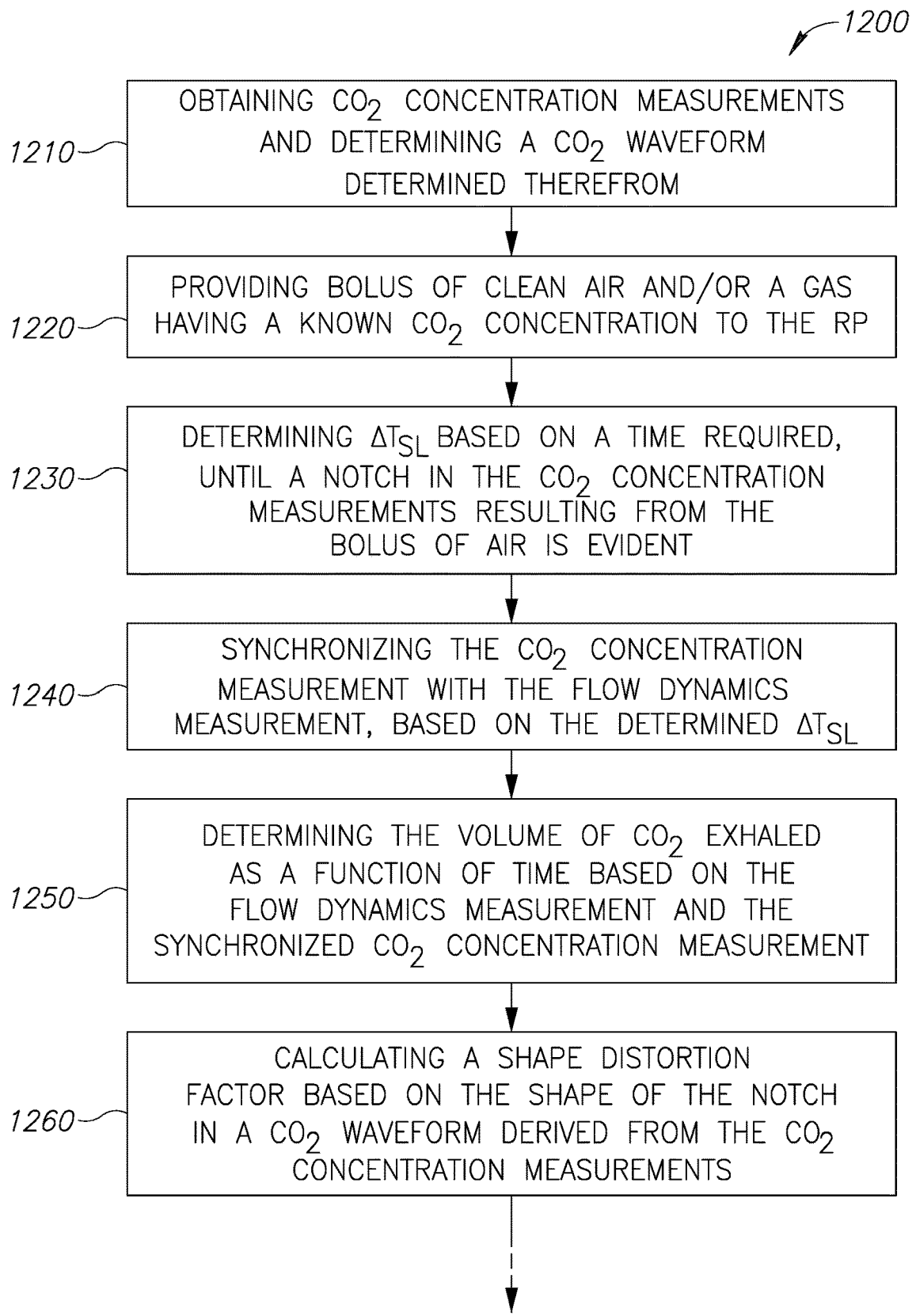
FIG. 12 is an illustrative flowchart of a method to perform volumetric side-stream capnograph, according to some embodiments.

Reference is now made to FIG. 12, which is an illustrative flowchart 1200 of a method for performing volumetric side-stream capnography, according to some embodiments. It is understood that certain steps are sequential whereas other steps may be performed either sequentially or simultaneously with other steps of the method.

At step 1210, flow dynamics measurements and $CO_2$ concentration measurements (and or $CO_2$ waveforms) are obtained. At step 1220 a bolus of clean air and/or a bolus of a gas having a known $CO_2$ concentration is provided. The bolus of air may be provided at initiation of inhalation ($T_i$), as further explained herein. This may be of particular importance when the air supplied is clean air from the ventilator. At step 1230 the duration of time ($\Delta T_{sl}$) required for a sample of gas to flow from a reference point to the side-stream $CO_2$ monitor is calculated based on a time required, until a notch in the $CO_2$ concentration measurements, resulting from the bolus of supplied air, is evident. At step 1240 a shape distortion factor is calculated based on the shape of the notch in the $CO_2$ waveform and, in step 1250 its deviation from an anticipated shape is determined, as described herein. In step 1260, the shape distortion factor may be utilized to cancel out distortions to the shape of the $CO_2$ waveform caused by friction of the sampling tube's wall on breath sample flow therein, thereby obtaining a correctly shaped $CO_2$ waveform. At step 1270, the $CO_2$ concentration measurement is synchronized in time with the flow dynamics measurement, based on the determined $\Delta T_{si}$; and in step 1280, the volume of $CO_2$ exhaled as a function of time is determined based on the flow dynamics measurement, the synchronized $CO_2$ concentration measurement and the correctly shaped $CO_2$ waveform.

The techniques may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A method for determining a volume of exhaled $CO_2$ as a function of time using side-stream capnography, the method comprising:
    obtaining flow dynamics measurements of a subject from a flow sensor;
    obtaining $CO_2$ concentration measurements of a subject from a side-stream $CO_2$ monitor;
    determining a duration of time ($\Delta T_{si}$) for a sample of gas to flow from a reference point to the side-stream $CO_2$ monitor, wherein determining of the $\Delta T_{si}$ is performed based on an on-start of inhalation ($T_i$) a duration of time between $T_i$ until the capnograph depicts a deflection in the $CO_2$ concentration measurements ($\Delta T_{TOTAL}$) and a time to wash away a gas volume encompassed between a Y-piece of a ventilator and the reference point RP ($\Delta T_{FLUSH}$), wherein ($\Delta T_{FLUSH}$) is calculated based on the inspiratory flow rate of the ventilator and the gas volume encompassed between the Y-piece of the ventilator and the RP
    synchronizing in time the $CO_2$ concentration measurement with the flow dynamics measurement, based on the determined $\Delta T_{si}$; and
    determining a volume of $CO_2$ exhaled as a function of time, based on the flow dynamics measurement and the synchronized $CO_2$ concentration measurement.

2. The method of claim 1, wherein the $T_i$ is derived from the flow dynamics measurements.

3. The method of claim 1, wherein the $\Delta T_{si}$ is calculated based on a difference in $\Delta T_{TOTAL}$ obtained when supplying the volume of air at at least two different flow rates.

4. The method of claim 1, wherein $T_i$ is determined based on the flow dynamics measurements.

5. A device for determining a volume of exhaled $CO_2$ as a function of time, the device comprising:
    a side-stream $CO_2$ monitor configured to measure $CO_2$ concentration over time; and
    a processor configured to:
        obtain flow dynamics measurements;
        obtain the $CO_2$ concentration measurements from the side-stream $CO_2$ monitor;
        determine a duration of time ($\Delta T_{si}$) for a sample of gas to flow from a reference point to the side-stream $CO_2$ monitor, wherein the processor is configured to determine the $\Delta T_{si}$ based on an inspiratory time ($\Delta T_{in}$) and a time to wash away a gas volume encompassed between a Y-piece of a ventilator and the RP ($\Delta T_{FLUSH}$), wherein ($\Delta T_{FLUSH}$) is calculated based on the inspiratory flow rate of the ventilator and the gas volume encompassed between the Y-piece of the ventilator and the RP;
        synchronize in time the $CO_2$ concentration measurement with the flow dynamics measurement based on the determined $\Delta T_{si}$; and
        determine a volume of $CO_2$ exhaled as a function of time based on the flow dynamics measurement and the synchronized $CO_2$ concentration measurement.

6. The device of claim 5, comprising a flow sensor configured to provide flow dynamics measurements.

7. The device of claim 5, wherein the processor is configured to calculate the $\Delta T_{in}$ based on a volume of air supplied by the ventilator and an inspiratory flow rate of the ventilator.

8. The device of claim 5, wherein the processor is configured to calculate the $\Delta T_{FLUSH}$ based on a difference in $\Delta T_{in}$ obtained when supplying the volume of air at at least two different flow rates.

9. The device of claim 5, wherein $T_i$ is determined based on the flow dynamics measurements.

* * * * *